US011690804B2

(12) United States Patent
Thibonnier

(10) Patent No.: US 11,690,804 B2
(45) Date of Patent: Jul. 4, 2023

(54) TARGETED DELIVERY OF THERAPEUTIC AGENTS TO HUMAN ADIPOCYTES

(71) Applicant: AptamiR Therapeutics, Inc., Naples, FL (US)

(72) Inventor: Marc Thibonnier, Naples, FL (US)

(73) Assignee: AptamiR Therapeutics, Inc., Naples, FL (US)

(*) Notice: Subject to any disclaimer, the term of this patent is extended or adjusted under 35 U.S.C. 154(b) by 66 days.

(21) Appl. No.: 17/250,317

(22) PCT Filed: Jul. 2, 2019

(86) PCT No.: PCT/US2019/040259
§ 371 (c)(1),
(2) Date: Jan. 4, 2021

(87) PCT Pub. No.: WO2020/010059
PCT Pub. Date: Jan. 9, 2020

(65) Prior Publication Data
US 2021/0145745 A1 May 20, 2021

Related U.S. Application Data

(60) Provisional application No. 62/810,141, filed on Feb. 25, 2019, provisional application No. 62/693,025, filed on Jul. 2, 2018.

(51) Int. Cl.
*A61K 9/127* (2006.01)
*A61K 47/54* (2017.01)
(Continued)

(52) U.S. Cl.
CPC .......... *A61K 9/127* (2013.01); *A61K 31/7088* (2013.01); *A61K 47/24* (2013.01);
(Continued)

(58) Field of Classification Search
CPC .... A61K 9/127; A61K 31/7088; A61K 47/24; A61K 47/28; A61K 47/543; A61K 47/64;
(Continued)

(56) References Cited

U.S. PATENT DOCUMENTS 5,013,830 A 5/1991 Ohtsuka et al.
5,149,797 A 9/1992 Pederson et al.
(Continued)

FOREIGN PATENT DOCUMENTS

WO WO 2017/187426 11/2017

OTHER PUBLICATIONS

Alexander et al., "MicroRNAs in adipogenesis and as therapeutic targets for obesity", *Expert Opin Ther Targets.*, 15(5):623-636, 2011.
(Continued)

*Primary Examiner* — Gollamudi S Kishore
(74) *Attorney, Agent, or Firm* — Norton Rose Fulbright US LLP

(57) ABSTRACT

Compositions and methods relating to modulating thermogenic regulation are disclosed. The compositions and methods can be used to treat diseases or conditions such as obesity or cardiometabolic disorders such as type 2 diabetes mellitus, NAFLD and NASH. Compositions include an adipocyte-targeting composition that includes a therapeutic agent capable of modulating thermogenic regulation, a targeting element facilitating cellular uptake and delivery of the therapeutic agent to a targeted adipocyte, and liposomal particles comprising sphingomyelin, DMPC, and cholesterol, wherein the liposomal particles enhance intra-cellular penetration of the therapeutic agent and protect the therapeutic agent from degradation.

24 Claims, 13 Drawing Sheets

(51) Int. Cl.
A61K 47/64 (2017.01)
A61K 31/7088 (2006.01)
A61K 47/24 (2006.01)
A61K 47/28 (2006.01)
C12N 15/113 (2010.01)

(52) U.S. Cl.
CPC ............ *A61K 47/28* (2013.01); *A61K 47/543* (2017.08); *A61K 47/64* (2017.08); *C12N 15/113* (2013.01); *C12N 2310/141* (2013.01); *C12N 2310/3513* (2013.01); *C12N 2310/3515* (2013.01); *C12N 2320/32* (2013.01)

(58) Field of Classification Search
CPC ...... A61K 9/0019; A61K 31/05; A61K 31/12; A61K 31/20; A61K 31/609; A61K 31/713; A61K 31/7105; A61K 47/542; A61K 47/6911; A61K 47/6913; C12N 15/113; C12N 2310/141; C12N 2310/3513; C12N 2310/3515; C12N 2320/32; C12N 2310/14; C12N 15/111; A61P 3/10; A61P 9/00; A61P 29/00
See application file for complete search history.

(56) References Cited

U.S. PATENT DOCUMENTS

| | | | |
|---|---|---|---|
| 5,220,007 | A | 6/1993 | Pederson et al. |
| 5,256,775 | A | 10/1993 | Froehler |
| 5,366,878 | A | 11/1994 | Pederson et al. |
| 5,403,711 | A | 4/1995 | Walder et al. |
| 5,491,133 | A | 2/1996 | Walder et al. |
| 5,565,350 | A | 10/1996 | Kmiec |
| 5,623,065 | A | 4/1997 | Cook et al. |
| 5,652,355 | A | 7/1997 | Metelev et al. |
| 5,652,356 | A | 7/1997 | Agrawal |
| 5,700,922 | A | 12/1997 | Cook |
| 7,759,318 | B1 | 7/2010 | Perera et al. |
| 9,034,839 | B2 | 5/2015 | Thibonnier |
| 2009/0291907 | A1 | 11/2009 | Esau et al. |
| 2013/0159091 | A1 | 6/2013 | Harper |

OTHER PUBLICATIONS

Bader et al., "Developing therapeutic microRNAs for cancer", *Gene Ther.*, 18(12):1121-1126, 2011.
Bozzuto et al., "Liposomes as nanomedical devices" *International Journal of Nanomedicine*, 10:975-999, 2015.
Broderick et al., "MicroRNA therapeutics", *Gene Ther.*, 18(12):1104-1110, 2011.
Czech et al., "RNAi-based therapeutic strategies for metabolic disease", *Nat Rev Endocrinol.*, 7(8):473-484, 2011.
Dahlman et al., "In vivo endothelial siRNA delivery using polymeric nanoparticles with low molecular weight." *Nat Nanotechnol.*, 9(8):648-655, 2014.
Davidson et al., "Current prospects for RNA interference-based therapies", *Nat Rev Genet.*, 12(5): 329-340, 2011.
Dong et al., "Lipopeptide nanoparticles for potent and selective siRNA delivery in rodents and nonhuman primates", *Proc Natl Acad Sci U S A.*, 111(11):3955-3960, 2014.
Ebert et al., "MicroRNA sponges: competitive inhibitors of small RNAs in mammalian cells", *Nature Methods*, 4(9):721-726, 2007.
Hardee, G.E., "Oral delivery of nucleic acid-based therapeutics", *Ther Deliv.*, 3(2):143-145, 2012.
International Search Report and Written opinion issued in corresponding International Application No. PCT/US19/40259 dated Sep. 20, 2019.
Lennox et al., "Chemical modification and design of anti-miRNA oligonucleotides", *Gene Ther.*, 18(12):1111-1120, 2011.
Li et al., "Therapeutic targeting of microRNAs: current status and future challenges", *Nat Rev Drug Discov.*, 13(8):622-638, 2014.
Maher et al., "Safety and efficacy of sodium caprate in promoting oral drug absorption: from in vitro to the clinic", *Adv Drug Deliv Rev.*, 61(15):1427-1449, 2009.
Mosa et al., "Hexarelin, a Growth Hormone Secretagogue, Improves Lipid Metabolic Aberrations in Nonobese Insulin-Resistant Male MKR Mice", *Endocrinology*, 158(10):3174-3187, 2017.
Snead et al., "RNA interference trigger variants: getting the most out of RNA for RNA interference-based therapeutics", *Nucleic Acid Ther.*, 22(3):139-146, 2012.
Thibonnier et al., "Metabolic Benefits of MicroRNA-22 Inhibition", *Nucleic Acid Ther.*, 30(2):104-116, 2020.
Thibonnier et al., "Metabolic and energetic benefits of microRNA-22 inhibition", *BMJ Open Diabetes Res Care.*, 8(1):e001478, 2020.
Thorsen SB et al., "The therapeutic potential of microRNAS in cancer", *Cancer J.*, 18(3):275-284, 2012.
Van Rooij et al., "Developing microRNA therapeutics", *Circ Res.*, 110(3):496-507, 2012.
Van Rooij et al., "Development of microRNA therapeutics is coming of age", *EMBO Mol Med.*, 6(7):851-864, 2014.
Webb et al., "Sphingomyelin-cholesterol liposomes significantly enhance the pharmacokinetic and therapeutic properties of vincristine in murine and human tumour modelsa", *Br J Cancer.*, 72(4):896-904, 1995.
Wittrup et al., "Knocking down disease: a progress report on siRNA therapeutics." *Nat Rev Genet.*, 16(9):543-552, 2015.
Xiao et al., "Novel approaches for gene-specific interference via manipulating actions of microRNAs: examination on the pacemaker channel genes HCN2 and HCN4", *Journal of Cellular Physiology*, 212(2):285-292, 2007.
Yu et al., "Insight into mechanisms of cellular uptake of lipid nanoparticles and intracellular release of small RNAs", *Pharm Res.*, 31(10):2685-2695, 2014.
Zatsepin et al., "Lipid nanoparticles for targeted siRNA delivery—going from bench to bedside", *Int J Nanomedicine*, 11:3077-3086, 2016.
Zhang et al., "Progress in microRNA delivery", *J Control Release.*, 172(3):962-974, 2013.

TARGETED DELIVERY OF THERAPEUTIC AGENTS TO HUMAN ADIPOCYTES

CROSS-REFERENCE TO RELATED APPLICATIONS

This application is a national phase application under 35 U.S.C. § 371 of International Application No. PCT/US2019/040259 filed Jul. 2, 2019, which claims the benefit of priority of U.S. Provisional Patent Application No. 62/693,025 filed Jul. 2, 2018, and U.S. Provisional Patent Application No. 62/810,141 filed Feb. 25, 2019, all of which are hereby incorporated by reference in their entirety.

BACKGROUND OF THE INVENTION

I. Field of the Invention

The invention generally concerns compositions comprising a therapeutic agent (oligonucleotide therapeutic such as a microRNA analog, small molecule, peptide, peptidomimetic, nutraceutical, or gene editing system) and methods for delivering such therapeutic agents to adipocytes for treatment of human obesity and related cardiometabolic disorders, including type 2 diabetes mellitus, Non-Alcoholic Fatty Liver Disease (NAFLD) and Non Alcoholic Steatohepatitis (NASH).

II. Description of Related Art

Obesity and overweight are growing global health problems. Obesity is the result of a chronic imbalance between energy intake and expenditure. This leads to storage of excess energy in the form of triglycerides in adipocytes, which typically exhibit both hypertrophy (increase in cell size) and hyperplasia (increase in cell number or adipogenesis). The recent worsening of obesity is due to the combination of excessive consumption of energy-dense foods high in saturated fats and sugars as well as reduced physical activity.

The current symptomatic medical treatments of obesity fail to achieve their long-term therapeutic goals, mainly due to limited drug efficacy and patients' poor adherence with lifestyle changes and therapies. Several obesity drugs have been removed from the market for safety reasons and small molecules currently in development are struggling to gain regulatory approval because of their modest short-term efficacy and unknown safety profile. Presently, only restrictive and malabsorptive bariatric surgery can achieve significant long-term reduction of weight excess with some favorable cardiovascular benefits. However, bariatric surgery creates a state of chronic digestive malabsorption. Accordingly, there is a need in the art for novel treatments for obesity.

NAFLD is a growing pandemic, affecting up to 31% of the adult human population worldwide, in relation with an increased prevalence of obesity and type 2 diabetes [1]. One hundred million Americans have a fatty liver, and most don't know it. Many will develop NAFLD, NASH, liver fibrosis, possibly end stage liver failure and cancer [2]. Without any currently approved therapy, NAFLD/NASH need safe and effective treatments. NAFLD/NASH is the major cause of chronic liver disease and it is associated with substantial morbidity and mortality in developed countries [3]. NAFLD is a fairly complex disease and a "multiple-hit" hypothesis is now proposed to explain the development of NAFLD [4]:

First hit: Lipid accumulation (steatosis)
Second hit: inflammation, mitochondrial dysfunction and oxidative stress (steatohepatitis)
Third hit: defective hepatocyte regeneration (fibrosis)

MicroRNAs (miRNAs) are attractive drug candidates for regulating cell fate decisions and improving complex diseases because the simultaneous modulation of many target genes by a single miRNA may provide effective therapies of multifactorial diseases like obesity, type 2 diabetes mellitus and NAFLD/NASH. As a matter of fact, miRNAs are extensive regulators of adipocyte differentiation, development and function and are viable therapeutic agents for obesity. Several miRNA agonists (agomirs) and antagonists (antagomirs) are currently in development to treat various human diseases, including cardiometabolic disorders. Examples of such agents are disclosed in U.S. Pat. No. 9,034,839 to Thibonnier. The technology platform to transform oligonucleotides into drugs has recently matured and several drugs are now in clinical development [5, 6]. However, targeted delivery to tissues/organs besides the liver has been seldom tested and could benefit from innovative approaches [7, 8].

There exists a need to achieve a targeted delivery of microRNA modulators and other therapeutic agents, including small molecules, peptides, peptidomimetics, nutraceuticals, and gene editing systems, to adipocytes, in order to optimize their long-term efficacy/safety profile, reduce cost of goods, and minimize off-target effects [9].

SUMMARY OF THE INVENTION

To achieve this goal, the inventors have developed various novel combinations of (a) therapeutic agents capable of modulating lipid oxidation and/or thermogenic regulation, such as miRNA agent compositions (e.g., miRNA agomirs and antagomirs), small molecules, peptides, peptidomimetics, nutraceuticals, and gene editing systems, (b) targeting elements (e.g., molecules transported by the Fatty Acid Transporter or antibodies recognizing the Fatty Acid Transporter) that bind to an adipocyte-specific cell surface marker, receptor, or transporter and facilitates cellular uptake and delivery of a thermogenic therapeutic agent to the targeted adipocyte, and (c) carrier or delivery nanoparticles that can deliver therapeutic agents to targeted adipocytes and enhance their intra-cellular penetration while protecting them from degradation. Compositions that employ such therapeutic agents, targeting elements, and carrier or delivery nanoparticles can be used in methods employing local subcutaneous administration (injection, patch or microneedles) of the therapeutic agents to the human adipose tissue, which results in minimizing systemic exposure and "off target effects," further improving therapeutic index, reducing cost of goods, and improving patients' convenience and adherence to treatment.

In some embodiments, disclosed herein is an adipocyte-targeting composition comprising: (a) a therapeutic agent capable of modulating lipid oxidation and/or thermogenic regulation; (b) a targeting element facilitating cellular uptake and delivery of the therapeutic agent to a targeted adipocyte; and (c) liposomal particles comprising sphingomyelin, DMPC, and cholesterol, wherein the liposomal particles enhance intra-cellular penetration of the therapeutic agent and protect the therapeutic agent from degradation. The liposomal particles can have a variety of formulations. In some embodiments, the cholesterol in the liposomal particles comprises 30-50% of the liposomal particles by weight, the DMPC comprises 30-50% of the liposomal particles by weight, and the cholesterol comprises 10-30% of the liposomal particles by weight. In some embodiments, the cholesterol comprises 40% of the liposomal particles by weight, the DMPC comprises 40% of the liposomal particles by weight, and the cholesterol comprises 20% of the liposomal particles by weight. In some embodiments, the liposomes have a peak mean diameter between about 135 and 150 nm or a polydispersity index of less than about 0.035.

The therapeutic agent in the composition can be one or a combination of a variety of lipid oxidation and/or thermogenic modulators, including for example, miRNA agomirs and antagomirs, small molecules, peptides, peptidomimetics, nutraceuticals, gene editing systems or any other agent capable of modulating lipid oxidation and/or thermogenesis. In some embodiments, the therapeutic agent comprises an RNA oligonucleotide from 7 to 14 nucleotides in length. In some embodiments, the therapeutic agent comprises miR-22 antagomir, miR-515 agomir, dinitrophenol, niclosamide, (β3 adrenergic receptor agonist, a thyromimetic agent, PPAR alpha agonist, PPAR gamma agonist, retinoic acid, hexarelin, thrombospondin-1 (TSP-1), prohibitin (PHB), a polyphenol, resveratrol, curcumin, a capsicinoid, an isoflavone, or a component of a gene editing system.

In some embodiments, the targeting element is a lipid. In some embodiments, the lipid is linked to the therapeutic agent. In some embodiments, the lipid comprises decanoic acid, dodecanoic acid, palmitic acid, stearic acid, oleic acid, oleoyl glycine, docosanoic acid, hexadecanoic acid, dotriacontahexaenoic acid, docosahexaenoic acid, or cholesterol. In some embodiments, the lipid is a fatty acid that is naturally transported by fatty acid translocase (FAT/CD36/SCARB3). In some embodiments, the therapeutic agent is linked to the lipid by a linker selected from the group consisting of a covalent bond, a disulfide bond, a diester bond, a peptide bond, an ionic bond, or a biotin-streptavidin bond.

In some embodiments, the targeting element specifically binds to Fatty Acid Translocase (FAT/CD36/SCARB3), Aquaporin 7 (AQP7), Perilipin 1 (PLIN1), or Perilipin 2 (PLIN2). In some embodiments, the targeting element comprises an antibody, antibody fragment, scFv, or single domain antibody. In some embodiments, the targeting element comprises Hexarelin (His-D-2-Me-Trp-Ala-Trp-D-Phe-Lys-NH2), or TSP-1, or a TSP-1 peptide having the amino acid sequence GVITRIR or VTCGVITRIR, or a PHB peptide having the amino acid sequence CKGGRAKDC. In some embodiments, the therapeutic agent is linked to the targeting element by a linker selected from the group consisting of a covalent bond, a disulfide bond, a diester bond, a peptide bond, an ionic bond, or a biotin-streptavidin bond.

In some embodiments, the therapeutic agent is encapsulated within the interior of the liposome. In some embodiments, the therapeutic agent is associated with the surface of the liposome. In some embodiments, the therapeutic agent is associated with the exterior surface of the liposome and is excluded from the interior of the liposome.

In some embodiments, therapeutic agent modulates respiratory chain uncoupling. In some embodiments, the therapeutic agent modulates the activity of UCP1, UCP2, or UCP3.

Also disclosed herein is an adipocyte-targeting therapeutic agent comprising a single-stranded oligonucleotide linked to Hexarelin via a disulfide bond. In some embodiments, the single-stranded oligonucleotide is between 7 and 14 nucleotides in length. In some embodiments, the single-stranded oligonucleotide is an antagomir of miR-22 or an agomir of miR-515.

Also disclosed herein is a method of modulating lipid oxidation and/or thermogenic regulation in a subject comprising providing to the subject any of the compositions described above. In some embodiments, providing the composition or therapeutic agent comprises injecting the composition or therapeutic agent subcutaneously, transcutaneously or intravenously. The method of modulating lipid oxidation and/or thermogenic regulation can be part of a strategy for treating a disease or condition. In some embodiments, the disease or condition is obesity or a cardiometabolic disorder such as type 2 diabetes mellitus, NAFLD and NASH.

In some embodiments, the patient receiving the composition has or has been diagnosed with obesity or a related cardiometabolic disorder such as type 2 diabetes mellitus, NAFLD and NASH.

DETAILED DESCRIPTION OF THE INVENTION

I. Definitions

Figure 1:
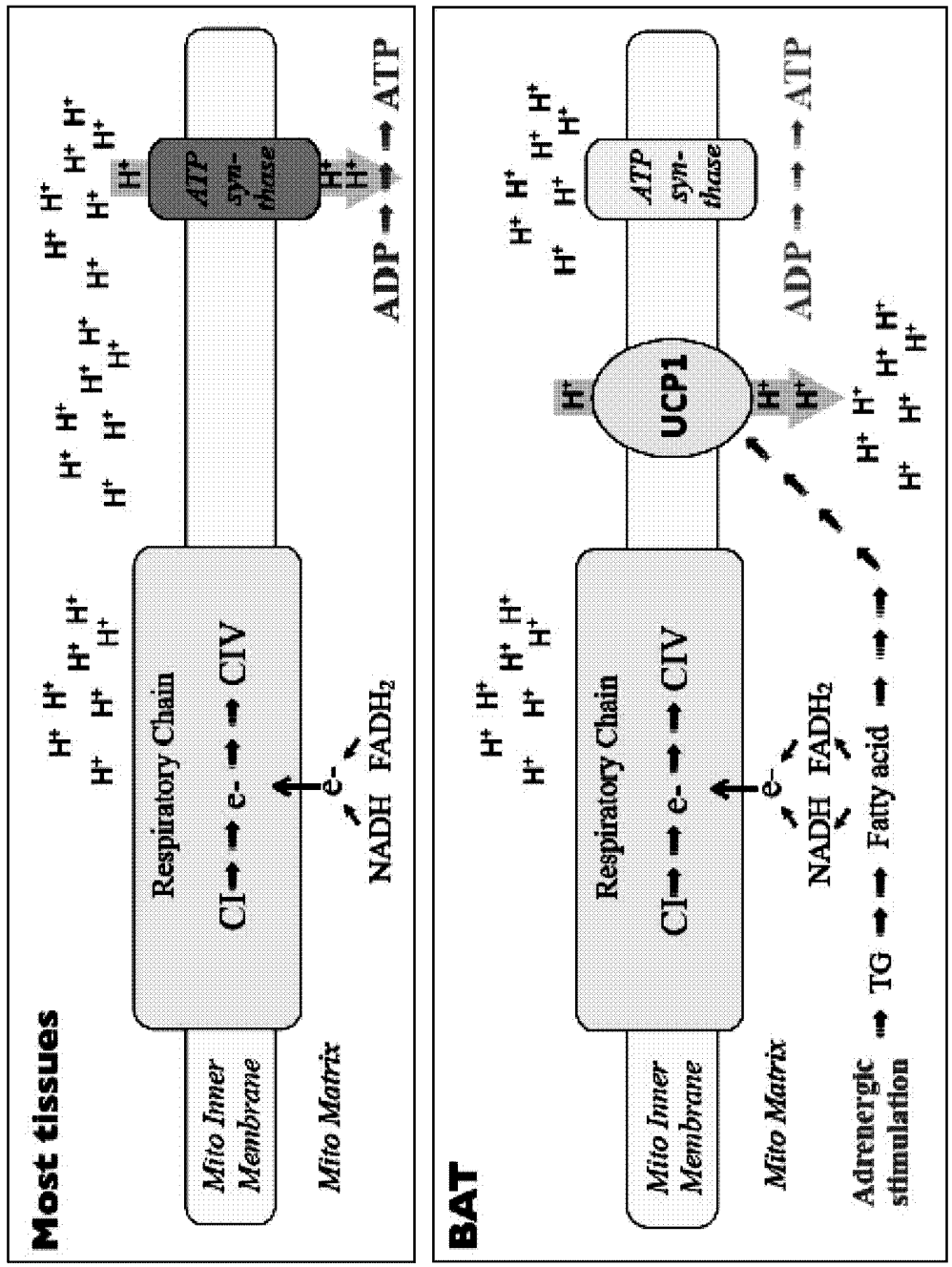
FIG. 1 is a schematic representation of the mitochondrial Respiratory Chain Complexes producing ATP (top panel) and Uncoupling of complexes IV and V by UCP1 in adipose tissue leading to thermogenesis/energy wasting (bottom panel).

Unless otherwise defined, all technical and scientific terms used herein have the same meaning as commonly understood by one of ordinary skill in the art to which this invention belongs. In case of conflict, the present application, including definitions, will control.

As used herein, the term "miRNA analog" refers to an oligonucleotide or oligonucleotide mimetic that directly or indirectly reprograms mesenchymal stem cells (ATMSCs) or white adipocytes (WAT) to become brown adipocytes (BAT). miRNA analogs can act on a target gene or an activator or repressor of a target gene, or on a target miRNA that directly or indirectly modulates the activity of a thermogenic regulator (e.g., a mitochondrial uncoupler or an activator or repressor thereof).

As used herein, the term "miRNA" refers to a single-stranded RNA molecule (or a synthetic derivative thereof), which is capable of binding to a target gene (either the mRNA or the DNA) and regulating expression of that gene. In certain embodiments, the miRNA is naturally expressed in an organism.

As used herein, the term "seed sequence" refers to a 6-8 nucleotide (nt) long substring within the first 8 nt at the 5'-end of the miRNA (i.e., seed sequence) that is an important determinant of target specificity.

As used herein, the term "agomir" refers to a synthetic oligonucleotide or oligonucleotide mimetic that functionally mimics a miRNA. An agomir can be an oligonucleotide with the same or similar nucleic acid sequence to a miRNA or a portion of a miRNA. In certain embodiments, the agomir has 1, 2, 3, 4, 5, 6, 7, 8, 9 or 10 nucleotide differences from the miRNA that it mimics. Further, agomirs can have the same length, a longer length or a shorter length than the miRNA that it mimics. In certain embodiments, the agomir has the same sequence as 6-8 nucleotides at the 5' end of the miRNA it mimics. In other embodiments, an agomir can be 5, 6, 7, 8, 9, 10, 11, 12, 13, 14, 15, 16, 17, 18, 19, 20, 21, or 22 nucleotides in length. In certain embodiments, agomirs include any of the sequences shown in miRBase. These chemically modified synthetic RNA duplexes include a guide strand that is identical or substantially identical to the miRNA of interest to allow efficient loading into the RISC complex, whereas the passenger strand is chemically modified to prevent its loading to the Argonaute protein in the RISC complex (Thorsen S B et al., Cancer J., 18(3):275-284 (2012); Broderick J A et al., Gene Ther., 18(12):1104-1110 (2011)).

As used herein, the term "antagomir" refers to a synthetic oligonucleotide or oligonucleotide mimetic having complementarity to a specific microRNA, and which inhibits the activity of that miRNA. The term "antimir" is synonymous with the term "antagomir". In certain embodiments, the antagomir has 1, 2, 3, 4, 5, 6, 7, 8, 9 or 10 nucleotide differences from the miRNA that it inhibits. Further, antagomirs can have the same length, a longer length or a shorter length than the miRNA that it inhibits. In certain embodiments, the antagomir hybridizes to 6-8 nucleotides at the 5' end of the miRNA it inhibits. In other embodiments, an antagomir can be 5, 6, 7, 8, 9, 10, 11, 12, 13, 14, 15, 16, 17, 18, 19, 20, 21 or 22 nucleotides in length. In certain embodiments, antagomirs include nucleotides that are complementary to any of the sequences shown in miRBase. The antagomirs are synthetic reverse complements that tightly bind to and inactivate a specific miRNA. Various chemical modifications are used to improve nuclease resistance and binding affinity. The most commonly used modifications to increase potency include various 2' sugar modifications, such as 2'-O-Methyl (2'-O-Me), 2'-O-methoxyethyl (2'-MOE), or 2'-fluoro (2'-F). The nucleic acid structure of the miRNA can also be modified into a locked nucleic acid (LNA) with a methylene bridge between the 2' oxygen and the 4' carbon to lock the ribose in the 3'-endo (North) conformation in the A-type conformation of nucleic acids (Lennox K A et al. Gene Ther. December 2011; 18(12):1111-1120; Bader A G et al. Gene Ther. December 2011; 18(12):1121-1126). This modification significantly increases both target specificity and hybridization properties of the molecules. Other modifications include 5'-(E)-Vinylphosphonate protection (5'-VP), backbone modifications (phosphorothioate (PS), Peptide Nucleic Acid (PNA), Phosphorodiamidate Morpholino Oligonucleotide (PMO), Ethylene-bridged Nucleic Acid (ENA), 5-Methylcytosine modification, introduction of a "pyrimidine cassette" and/or introduction of a "DNA gap".

As used herein, the term "interfering RNA" refers to any double stranded or single stranded RNA sequence capable of inhibiting or down regulating gene expression by mediating RNA interference. Interfering RNAs, include are not limited, to small interfering RNA ("siRNA") and small hairpin RNA ("shRNA"). "RNA interference" refers to the selective degradation of a sequence-compatible messenger RNA transcript.

As used herein, the term "small interfering RNA" or "siRNA" refers to any small RNA molecule capable of inhibiting or down regulating gene expression by mediating RNA interference in a sequence specific manner. The small RNA can be, for example, about 16 to 21 nucleotides long.

As used herein, the term "shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA (siRNA) by a cleavage event mediated by the enzyme Dicer, which is a member of the RNase III family.

As used herein, the term "antisense oligonucleotide" refers to a synthetic oligonucleotide or oligonucleotide mimetic that is complementary to a DNA or mRNA sequence (e.g., a miRNA).

As used herein, the term "miR-mask" refers to a single stranded antisense oligonucleotide that is complementary to a miRNA binding site in a target mRNA, and that serves to inhibit the binding of miRNA to the mRNA binding site. See, e.g., Xiao, et al. "Novel approaches for gene-specific interference via manipulating actions of microRNAs: examination on the pacemaker channel genes HCN2 and HCN4," Journal of Cellular Physiology, vol. 212, no. 2, pp. 285-292, 2007, which is incorporated herein in its entirety.

As used herein, the term "miRNA sponge" refers to a synthetic nucleic acid (e.g. a mRNA transcript) that contains multiple tandem-binding sites for a miRNA of interest, and that serves to titrate out the endogenous miRNA of interest, thus inhibiting the binding of the miRNA of interest to its endogenous targets. See, e.g., Ebert et al., "MicroRNA sponges: competitive inhibitors of small RNAs in mammalian cells," Nature Methods, vol. 4, no. 9, pp. 721-726, 2007, which is incorporated herein in its entirety.

As used herein, the term "respiratory chain uncoupling" refers to the dissipation of the mitochondrial inner membrane proton gradient, thereby preventing the synthesis of ATP in the mitochondrion by oxidative phosphorylation.

As used herein, the term "mitochondrial uncoupler" refers to a protein (or the encoding nucleic acid) that can dissipate of the mitochondrial inner membrane proton gradient, thereby preventing the synthesis of ATP in the mitochondrion by oxidative phosphorylation. Exemplary mitochondrial uncouplers include UCP1, UCP2 and UCP3.

As used herein, the terms "activator" or "repressor" of a mitochondrial uncoupler refers to a protein that serves to upregulate or downregulate, respectively, an activity of a mitochondrial uncoupler.

As used herein, the term "thermogenic regulator" refers to a therapeutic agent (oligonucleotide, small molecule, peptide, peptidomimetic, or gene editing system) that regulates thermogenesis either directly or indirectly. The term encompasses mitochondrial uncouplers and also activators and repressors of mitochondrial uncouplers.

As used herein, the term "modulate" refers to increasing or decreasing a parameter. For example, to modulate the activity of a protein, that protein's activity could be increased or decreased.

As used herein, the term "activity" of mitochondrial uncoupler or thermogenic regulator refers to any measurable biological activity including, without limitation, mRNA expression, protein expression, or respiratory chain uncoupling.

The "effective amount" of a composition or therapeutic agent is an amount sufficient to be effective in treating or preventing a disorder or to regulate a physiological condition in humans.

As used herein, "cardio-metabolic disorders" include cardiovascular diseases, stroke, diabetes mellitus, dyslipidemia, metabolic syndrome, and hepatic steatosis.

A "subject" is a vertebrate, including any member of the class Mammalia, including humans, domestic and farm animals, and zoo, sports or pet animals, such as mouse, rabbit, pig, sheep, goat, cattle and higher primates.

The term "mammal" refers to any species that is a member of the class Mammalia, including rodents, primates, dogs, cats, camelids and ungulates. The term "rodent" refers to any species that is a member of the order rodentia including mice, rats, hamsters, gerbils and rabbits. The term "primate" refers to any species that is a member of the order primates, including monkeys, apes and humans. The term "camelids" refers to any species that is a member of the family camelidae including camels and llamas. The term "ungulates" refers to any species that is a member of the superorder ungulata including cattle, horses and camelids. According to some embodiments, the mammal is a human.

"Treatment", or "treating" as used herein, is defined as the application or administration of a therapeutic agent (e.g., oligonucleotide, small molecule, peptide, peptidomimetic, nutraceutical, or gene editing system) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

"Pharmacogenomics", as used herein, refers to the application of genomics technologies such as gene sequencing, statistical genetics, and gene expression analysis to drugs in clinical development and on the market More specifically, the term refers to the study of how a patient's genes determine his or her response to a drug (e.g., a patient's "drug response phenotype", or "drug response genotype").

II. Regulation of Gene Expression by RNA Agents

Figure 2:
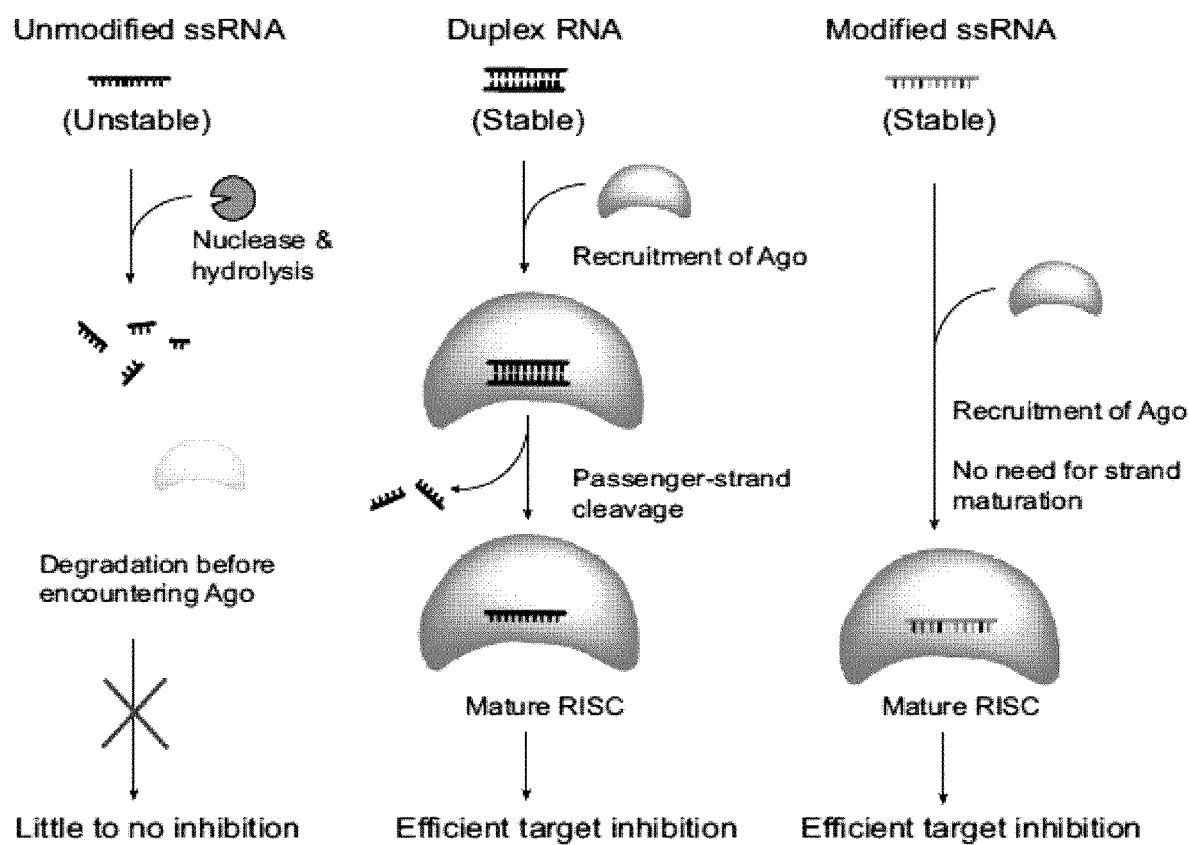
FIG. 2 illustrates mechanisms of action of chemically modified ss-miRNAs [10].
Figure 3:
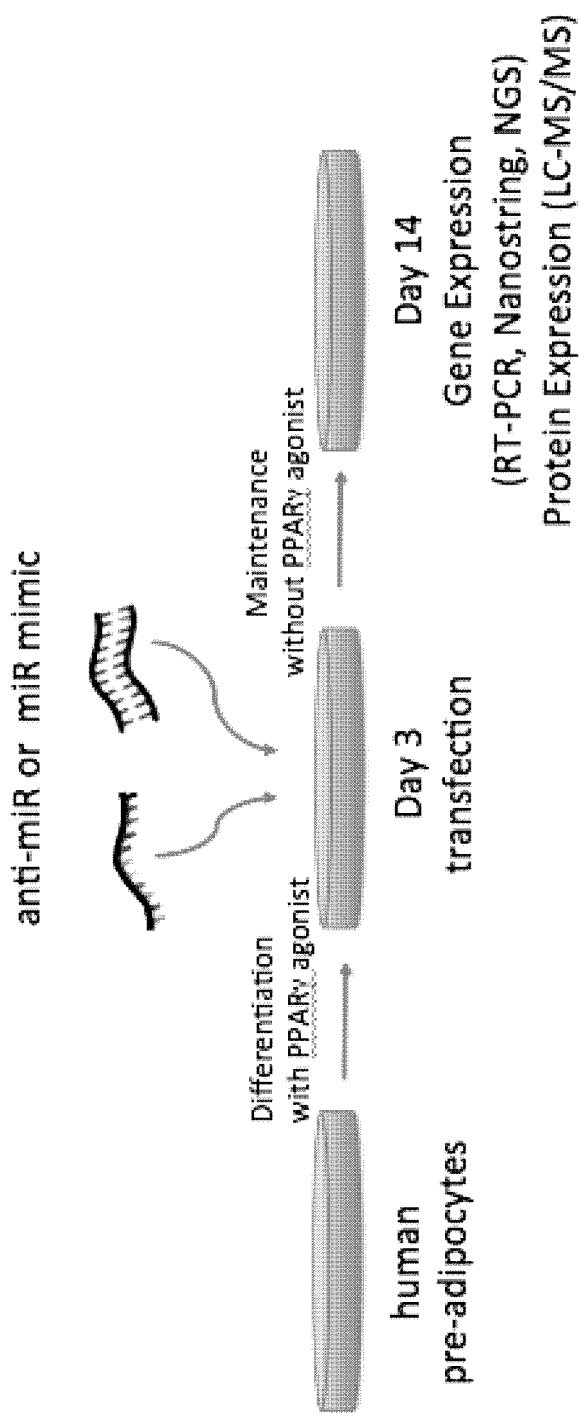
FIG. 3 shows an experimental design for testing RNA-based therapeutic agents in human adipocytes cultures.

MicroRNAs (miRNAs) are small non-coding RNAs that bind to complementary messenger RNAs (mRNAs) and subsequently regulate protein expression [12]. Each miRNA is evolutionarily selected to modulate the expression of gene pathways. miRNAs are synthesized as long single-stranded RNAs (pri-miRNA) that fold into hairpin loop structures (pre-miRNA). These hairpins are processed by the enzymes drosha and dicer into double-stranded mature miRNAs. The guide strand complementary to target mRNA transcripts is loaded into argonaute (AGO) proteins while the passenger strand is removed [13]. The guide strand/AGO complex then binds by sequence complementarity to targets that are typically located within 3'-untranslated regions (3'-UTR) of mRNAs.

miRNA inhibitors (antagomirs) are engineered single-stranded oligonucleotides that bind to complementary miRNAs through Watson-Crick base-pairing, blocking their interaction with target mRNAs. To improve the structure-activity relationship of miRNA inhibitors, the following chemical modifications may be implemented. The phosphates in the backbone are replaced by phosphorothioates to inhibit nuclease degradation and promote plasma protein binding, thus extending circulation time and tissue distribution. Modifications to the 2' carbon of the sugar group (2'-Fluor, 2'-O-methyl, 2'-methoxyethyl) and Locked Nucleic Acid (LNA) conformations are also used to inhibit nuclease degradation, increase affinity to target RNAs, and blunt the immune response to foreign DNA and RNA [5]. Phosphorothioate backbone modified oligonucleotides can be administered subcutaneously in saline without additional formulation (the so called "naked miRNA inhibitors"), and generally have similar and predictable pharmacokinetics. The initial distribution is rapid, with a circulating $t_{1/2}$ of a few hours, and a bioavailability over 90%. Delivery to the liver, kidney, adipose tissue, spleen, and bone marrow is robust, with much lower amounts found in heart and muscle. These compounds do not cross the blood-brain barrier.

miRNA mimics (agomirs) are chemically modified versions of the native miRNAs that can be loaded into the RISC complex to bind and regulate target mRNAs via their "guide" strand while the complementary "passenger" strand is degraded. Chemical modifications are used to protect the miRNA mimic from nuclease degradation and improve potency, but the patterns of optimal chemical modification may be different from siRNA and from single-stranded miRNA inhibitors. Synthetic chemically modified single-stranded miRNAs (ss-miRNAs) can mimic the functions of double-stranded miRNAs to silence the expression of target genes, as illustrated in FIG. 2 [14, 15]. Such action requires the recruitment of the argonaute 2 (AGO2) protein to the target transcripts. Modified ss-miRNA mimics can combine the power of function through the RNAi pathway with the more favorable pharmacological properties of single stranded oligonucleotides. In vivo effects of ss-miRNAs in animals were achieved after systemic or local administration [14, 16, 17]. The inventors have developed targeting strategies that effectively deliver single- and double-stranded miRNAs to adipocytes.

III. Thermogenic Modulator Elements

In certain aspects, the compositions disclosed herein comprise therapeutic agents for modulating thermogenesis. Exemplary thermogenic regulators are set forth in Table 1 herein.

TABLE 1

Thermogenic Modulators:

| Therapeutic Class | Compound |
|---|---|
| Oligonucleotide | miR-22 antagomir |
| Oligonucleotide | miR-515 agomir |
| Small molecule | Dinitrophenol |

TABLE 1-continued

Thermogenic Modulators:

| Therapeutic Class | Compound |
|---|---|
| Small molecule | Niclosamide |
| Small molecule | Beta3 adrenergic receptor agonist |
| Small molecule | Thyromimetic agent |
| Small molecule | PPAR Alpha agonist |
| Small molecule | PPAR Gamma agonist |
| Small molecule | Retinoic Acid |
| Peptide/peptidomimetic | Hexarelin |
| Peptide/peptidomimetic | Thrombospondin-1 (TSP-1) |
| Peptide/peptidomimetic | Prohibitin (PHB) |
| Nutraceutical | Polyphenols (e.g. Resveratrol) |
| Nutraceutical | Curcumin |
| Nutraceutical | Capsicinoids |
| Nutraceutical | Green Tea Extracts (e.g. EGCG) |
| Nutraceutical | Isoflavones (e.g. Genistein) |
| Nutraceutical | Quercetin |
| Gene Editing System | Gene Editing of Single Nucleotide Polymorphism (SNPs) located in the promoter region of the UCP1 gene and linked to the risk of obesity and diabetes |
| Gene Editing System | Gene Editing repression or activation of transcription factors modulating UCP1 gene expression |
| Gene Editing System | Epigenetic reduction of UCP1 gene methylation |

In exemplary embodiments, the thermogenic modulator such as a miRNA analog modulates the activity of at least one mitochondrial uncoupler (e.g., UCP1, UCP2 and/or UCP3). Such methods and compositions are particularly useful for treating obesity. See U.S. Pat. No. 9,034,839 and International Application Serial No. PCT/US2013/037579 filed on Apr. 22, 2013, each of which hereby incorporated by reference. See FIG. 1 for a schematic representation of the mitochondrial respiratory chain complexes and the uncoupling of complexes IV and V by UCP1.

Mitochondrial uncoupling proteins (UCP) are members of the family of mitochondrial anion carrier proteins (MACP). UCPs separate oxidative phosphorylation from ATP synthesis with energy dissipated as heat (also referred to as the "mitochondrial proton leak"). UCPs facilitate the transfer of anions from the inner to the outer mitochondrial membrane and the return transfer of protons from the outer to the inner mitochondrial membrane generating heat in the process. UCPs are the primary proteins responsible for thermogenesis and heat dissipation. Uncoupling Protein 1 (UCP1), also named thermogenin, is a BAT specific protein responsible for thermogenesis and heat dissipation. UCP2 is another Uncoupling Protein also expressed in adipocytes. UCP3 is mostly expressed in skeletal muscle. UCPs are part of network of thermogenic regulator proteins.

Modulation of thermogenic regulators to induce BAT differentiation and/or mitochondrial uncoupling provides a method to induce thermogenesis in a subject and, hence, to treat obesity. However, chemical pharmacologic approaches cannot target these molecules, as they do not belong to the classic 'target classes' (kinases, ion channels, G-protein coupled receptors, etc.) that dominate the 'druggable space' of traditional drug discovery. Accordingly, the compositions and methods disclosed herein modulate these thermogenic regulators using miRNA agents.

In certain embodiments, miRNA modulators or other therapeutic agents are employed to upregulate the activity of a mitochondrial uncoupler (e.g., the mRNA expression level, protein expression level, or mitochondrial uncoupling activity). Upregulation of a mitochondrial uncoupler can be achieved in several ways. In one embodiment, a miRNA analog directly inhibits the activity of a naturally occurring miRNA that is responsible for downregulation of the activity (e.g., the mRNA expression level, protein expression level) of the mitochondrial uncoupler. In certain embodiments, the miRNA agent directly binds to the mRNA or promoter region of the mitochondrial uncoupler. For example, the miRNA agent may directly bind to the 5' UTR or coding sequence of the mRNA of at least one mitochondrial uncoupler.

In certain embodiments, the miRNA agent or other therapeutic agent modulates the activity of an activator or repressor of a mitochondrial uncoupling protein. In another embodiment, a miRNA analog upregulates the activity (e.g., the mRNA expression level, protein expression level) of an activator of the mitochondrial uncoupler. This upregulation can be achieved, for example, by directly inhibiting the activity of a naturally occurring miRNA that is responsible for downregulation of the expression of the activator. In other embodiments, the miRNA analog downregulates the activity (e.g., the mRNA expression level, protein expression level) of a repressor of the mitochondrial uncoupler. This downregulation can be achieved, for example, by directly inhibiting the expression of a repressor of a mitochondrial uncoupler using a miRNA analog.

In certain embodiments, the compositions and methods disclosed herein employ miRNA analogs or other therapeutic agents for the modulation of thermogenic regulators (e.g., mitochondrial uncouplers, such as UCP1). miRNA analogs, suitable for use in the methods disclosed herein, included, without limitation, miRNA, agomirs, antagomirs, miR-masks, miRNA-sponges, siRNA (single- or double-stranded), shRNA, antisense oligonucleotides, ribozymes, or other oligonucleotide mimetics which hybridize to at least a portion of a target nucleic acid and modulate its function.

In certain embodiments, the miRNA analogs are miRNA molecules or synthetic derivatives thereof (e.g., agomirs). In one particular embodiment, the miRNA analog is a miRNA. miRNAs are a class of small (e.g., 18-24 nucleotides) non-coding RNAs that exist in a variety of organisms, including mammals, and are conserved in evolution. miRNAs are processed from hairpin precursors of about 70 nucleotides which are derived from primary transcripts through sequential cleavage by the RNAse III enzymes drosha and dicer. Many miRNAs can be encoded in intergenic regions, hosted within introns of pre-mRNAs or within ncRNA genes. Many miRNAs also tend to be clustered and transcribed as polycistrons and often have similar spatial temporal expression patterns. In general, miRNAs are post-transcriptional regulators that bind to complementary sequences on a target gene (mRNA or DNA), resulting in gene silencing by, e.g., translational repression or target degradation. One miRNA can target many different genes simultaneously.

Exemplary miRNA molecules for use in the disclosed methods include without limitation those selected from the group consisting of hsa-miR-1-1, hsa-miR-1-2, miR-19a-b, hsa-miR-105, hsa-miR-1283, hsa-mir-129, hsa-miR-133a-1, hsa-miR-133a-2, hsa-miR-143, hsa-mir-143-5p, hsa-mir-147, hsa-mir-149, hsa-mir-199a, hsa-mir-199b, hsa-mir-200c, hsa-mir-204, hsa-mir-205, hsa-miR-206, hsa-mir-21, hsa-mir-211, hsa-mir-218, hsa-mir-218-1, hsa-mir-218-2, hsa-mir-219-2, hsa-mir-219-2-3p, hsa-mir-22, hsa-mir-22-3p, hsa-mir-22-5p, hsa-mir-24-2, hsa-miR-30a-e, hsa-miR-3177-5p, hsa-mir-325, hsa-mir-331, hsa-mir-331-5p, hsa-miR-3613-3p, hsa-mir-362, hsa-mir-362-5p, hsa-miR-3658, hsa-mir-367, hsa-mir-371, hsa-mir-371-5p, hsa-mir-377, hsa-mir-378, hsa-mir-378a-5p, hsa-mir-382, hsa-mir-383, hsa-mir-422a, hsa-mir-425, hsa-miR-455-3p, hsa-miR-455-5p, hsa-miR-491, hsa-mir-508, hsa-mir-508-5p, hsa-mir-512-1, hsa-mir-512-2, hsa-miR-515-3p, hsa-mir-519e, hsa-miR-520a, hsa-mir-543, hsa-mir-545, hsa-mir-549, hsa-mir-556, and hsa-miR-568, hsa-mir-620, hsa-mir-643, hsa-mir-654-3p, hsa-miR-7a-g, hsa-mir-765, hsa-mir-871, hsa-mir-888, hsa-mir-888-3p, hsa-mir-92b, hsa-mir-93, hsa-mir-96, and hsa-mir-99a.

Additional miRNAs that modulate regulator molecules may be identified using publicly available Internet tools that predict miRNA targets. Modulation of a single miRNA can promote the formation of adipocytes from adipogenic precursor cells. Pathway-specific miRNAs that target multiple genes within one discrete signaling pathway are preferred, rather than universal miRNAs that are involved in many signaling pathways, functions or processes.

In another particular embodiment, the miRNA analog is an agomir. Agomirs of a particular miRNA can be identified using the screening methods disclosed herein. In one particular embodiment, the agomir is a functional mimetic of human miR-22 (Davidson B L et al., Nat. Rev. Genet., 12(5):329-340 (2011).

In certain embodiments, the miRNA analogs are oligonucleotide or oligonucleotide mimetics that inhibit the activity of one or more miRNA. Examples of such molecules include, without limitation, antagomirs, interfering RNA, antisense oligonucleotides, ribozymes, miRNA sponges and miR-masks. In one particular embodiment, the miRNA analog is an antagomir. In general, antagomirs are chemically modified antisense oligonucleotides that bind to a target miRNA and inhibit miRNA function by prevent binding of the miRNA to its cognate gene target. Antagomirs can include any base modification known in the art. In one particular embodiment, the antagomir inhibits the activity of human miR-22 (van Rooij E et al., Circ. Res., 110(3):496-507 (2012); Snead N M et al., Nucleic Acid Ther., 22(3): 139-146 (2012); Czech M P et al., Nat. Rev. Endocrinol., 7(8):473-484 (2011).

In certain embodiments, the miRNA analogs are 8 to 50 nucleotides in length. One having ordinary skill in the art will appreciate that this embodies oligonucleotides having antisense portions of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within.

In certain embodiments, the miRNA analogs are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids may be formed as composite structures of two or more oligonucleotides, modified oligonucleotides, oligonucleosides, and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

In certain embodiments, the miRNA analogs comprise at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, a basic residue or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make an oligonucleotide more resistant to nuclease digestion, thereby prolonging in vivo half-life. Specific examples of modified oligonucleotides include those comprising backbones comprising, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, ~N($CH_3$)~O~$CH_2$ (known as a methylene(methylimino) or MMI backbone), $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH; amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497), each of which is herein incorporated by reference in its entirety. Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3' alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference in its entirety. Morpholino-based oligomeric compounds are known in the art described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991, each of which is herein incorporated by reference in its entirety. Cyclohexenyl nucleic acid oligonucleotide mimetics are described in Wang et al., J. Am. Chem. Soc., 2000, 122, 8595-8602, the contents of which is incorporated herein in its entirety.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference in its entirety.

In certain embodiments, miRNA analogs comprise one or more substituted sugar moieties, e.g., one of the following at the 2' position: OH, SH, $SCH_3$, F, OCN, $OCH_3$, $OCH_3$, $OCH_3$ $O(CH_2)_n$ $CH_3$, $O(CH_2)_n$ $NH_2$ or $O(CH_2)_n$ $CH_3$ where n is from 1 to about 10; Ci to CIO lower alkyl, alkoxyalkoxy, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacokinetic/pharmacodynamic properties of an oligonucleotide and other substituents having similar properties. A preferred modification includes 2'-methoxyethoxy [2'-O-$CH_2CH_2OCH_3$, also known as 2'-O-(2-methoxyethyl)]. Other preferred modifications include 2'-methoxy (2'-O—$CH_3$), 2'-propoxy (2'-$OCH_2$ $CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

In certain embodiments, miRNA analogs comprise one or more base modifications and/or substitutions. As used herein, "unmodified" or "natural" bases include adenine (A), guanine (G), thymine (T), cytosine (C) and uracil (U). Modified bases include, without limitation, bases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic bases, e.g., 2-aminoadenine, 2-(methylamino)adenine, 2-(imidazolylalkyl)adenine, 2-(aminoalklyamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine (Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, can also be included. 5-Me-C substitutions can also be included. These have been shown to increase nucleic acid duplex stability by 0.6-1.2OC (Sanghvi, Y. S., in Crooke, S. T. and Lebleu, B., eds., Antisense Research and Applications, CRC Press, Boca Raton, 1993, pp. 276-278). Further suitable modified bases are described in U.S. Pat. Nos. 3,687,808, 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

It is not necessary for all positions in a given oligonucleotide to be uniformly modified, and in fact more than one of the aforementioned modifications may be incorporated in a single oligonucleotide or even at within a single nucleoside within an oligonucleotide.

In certain embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen et al., Science, 1991, 254, 1497-1500.

In certain embodiments, the miRNA agent or other therapeutic agent is linked (covalently or non-covalently) to one or more moieties or conjugates that enhance the activity, cellular distribution, or cellular uptake of the oligonucleotide. Such moieties include, without limitation, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937), each of which is herein incorporated by reference in its entirety. See also U.S. Pat. Nos. 4,828,979; 4,948,882; 5,218,105; 5,525, 465; 5,541,313; 5,545,730; 5,552,538; 5,578,717; 5,580, 731; 5,580,731; 5,591,584; 5,109,124; 5,118,802; 5,138, 045; 5,414,077; 5,486, 603; 5,512,439; 5,578,718; 5,608, 046; 4,587,044; 4,605,735; 4,667,025; 4,762,779; 4,789, 737; 4,824,941; 4,835,263; 4,876,335; 4,904,582; 4,958, 013; 5,082,830; 5,112,963; 5,214,136; 5,082,830; 5,112, 963; 5,214,136; 5,245,022; 5,254,469; 5,258,506; 5,262, 536; 5,272,250; 5,292,873; 5,317,098; 5,371,241, 5,391, 723; 5,416,203, 5,451,463; 5,510,475; 5,512,667; 5,514, 785; 5,565,552; 5,567,810; 5,574,142; 5,585,481; 5,587, 371; 5,595,726; 5,597,696; 5,599,923; 5,599,928 and 5,688, 941, each of which is herein incorporated by reference in its entirety.

The miRNA analogs must be sufficiently complementary to the target mRNA, i.e., hybridize sufficiently well and with sufficient specificity, to give the desired effect "Complementary" refers to the capacity for pairing, through hydrogen bonding, between two sequences comprising naturally or non-naturally occurring bases or analogs thereof. For example, if a base at one position of a miRNA analog is capable of hydrogen bonding with a base at the corresponding position of a target nucleic acid sequence, then the bases are considered to be complementary to each other at that position. In certain embodiments, 100% complementarity is not required. In other embodiments, 100% complementarity is required.

miRNA analogs for use in the methods disclosed herein can be designed using routine methods. Additional target segments are readily identifiable by one having ordinary skill in the art in view of this disclosure. Target segments of 5, 6, 7, 8, 9, 10 or more nucleotides in length comprising a stretch of at least five (5) consecutive nucleotides within the seed sequence, or immediately adjacent thereto, are considered to be suitable for targeting a gene. In some embodiments, target segments can include sequences that comprise at least the 5 consecutive nucleotides from the 5'-terminus of one of the seed sequence (the remaining nucleotides being a consecutive stretch of the same RNA beginning immediately upstream of the 5'-terminus of the seed sequence and continuing until the miRNA agent contains about 5 to about 30 nucleotides). In some embodiments, target segments are represented by RNA sequences that comprise at least the 5 consecutive nucleotides from the 3'-terminus of one of the seed sequence (the remaining nucleotides being a consecutive stretch of the same miRNA beginning immediately downstream of the 3'-terminus of the target segment and continuing until the miRNA agent contains about 5 to about 30 nucleotides). One having skill in the art armed with the sequences provided in U.S. Pat. No. 9,034,839 will be able, without undue experimentation, to identify further preferred regions to target using miRNA analogs. Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target nucleic acid sequences), to give the desired effect.

In certain embodiments, miRNA agents used in the compositions and methods disclosed herein are expressed from a recombinant vector. Suitable recombinant vectors include, without limitation, DNA plasmids, viral vectors or DNA minicircles. Generation of the vector construct can be accomplished using any suitable genetic engineering techniques well known in the art. In certain embodiments, miRNA agents are synthesized in vitro using chemical synthesis techniques.

In certain embodiments, thermogenic modulator elements are from the therapeutic class of small molecules which have been demonstrated to increase thermogenesis and browning of adipocytes after oral administration. They include dinitrophenol, Beta3 adrenergic receptor agonists, thyromimetic agents, PPAR Alpha agonists and PPAR Gamma agonists. Unfortunately, their systemic administration trigger adverse reactions that preclude their regulatory approval for therapeutic use. It is theorized that targeted delivery of much smaller quantities of these small molecules to the adipose tissues will produce the desired thermogenic effect while avoiding off targets and toxic effects.

In certain embodiments, thermogenic modulator elements are from the therapeutic class of nutraceuticals which have been demonstrated to increase thermogenesis and browning of adipocytes after oral administration. They include polyphenols (e.g. Resveratrol), Curcumin, capsicinoids, quercetin, isoflavones (e.g. Genistein), and Green Tea Extracts (e.g., Epigallocatechin gallate or EGCG).

It is expected that targeted delivery of much smaller quantities of these nutraceuticals to the adipose tissues according to the compositions and methods disclosed herein will produce the desired thermogenic effect while avoiding off targets and toxic effects.

In certain embodiments, thermogenic modulator elements are from the therapeutic class of gene editing systems which potentially increase thermogenesis and browning of adipocytes. They include Gene Editing of Single Nucleotide Polymorphism (SNPs) located in the promoter region of the UCP1 gene and linked to the risk of obesity and diabetes, Gene Editing repression or activation of transcription factors modulating UCP1 gene expression and Epigenetic reduction of UCP1 gene methylation. For obvious safety reasons, these gene editing systems have to be delivered specifically to the adipocyte tissues where their effects should be confined.

IV. Adipose-Specific Targeting

As stated previously, the present disclosure provides compositions and methods for targeted delivery of thermogenic modulators to adipose tissue, e.g., white adipose tissue (WAT). Specifically, compositions and agents disclosed herein selectively deliver thermogenic modulators to the adipose tissue. Human subcutaneous adipose tissue contains several cell types, any of which may be selectively targeted with compositions disclosed herein. For example, in certain embodiments, the target cell is an adipocyte. In other embodiments, the target cell may be an adipocyte precursor such as a pre-adipocyte or adipose tissue mesenchymal stem cell (ATMSC). ATMSCs possess the ability to differentiate into multiple lineages, such as adipocytes, osteocytes, and chondrocytes and are present in human subcutaneous adipose tissue in appreciable quantities. Human ATMSCs can be reprogrammed to become brown adipocytes (BAT) via modulation of a defined set of transcription factors.

In some embodiments, compositions bind to an adipose-target cell comprising one or more ATMSC-positive surface markers. Exemplary ATMSC-positive surface markers include aquaporin 7 (AQP7), CD9 (tetraspan), CD10 (MME), CD13 (ANPEP), CD29 (β-1 integrin), CD36 (FAT/SCARB3), CD44 (hyaluronate), CD49d (α-4 integrin), CD54 (ICAM-1), CD55 (DAF), CD59, CD73 (SH3), CD90 (Thy1), CD91 (LPR1), CD105 (SH2, Endoglin), CD137, CD146 (Muc 18), CD166 (ALCAM), and HLA-ABC.

In some embodiments, compositions selectively bind to subcutaneous or white adipose tissue (WAT). By selectively binding to WAT, compositions can facilitate targeted delivery of thermogenic miRNA modulators which promote conversion of white adipocyte to thermogenic brite or brown or beige adipocytes (BAT). Exemplary WAT-positive markers include adiponectin, aquaporin 7 (AQP7), caveolin-1, caveolin-2, CD36 (FAT/SCARB3), CLH-22 (clathrin heavy chain chr. 22), FABP4 (adipocyte protein 2, ap2), SLC27A1

(FATP1), SLC27A2 (FATP2), GLUT4 (glucose transporter 4), perilipin 1, perilipin 2, and resistin.

In some embodiments, compositions bind to an adipose target cell comprising cellular markers (including several lipid transporters) that are preferentially expressed at the surface of adipocytes. Exemplary adipocyte cellular markers include aquaporin 7 (AQP7), caveolin-1 (CAV1), caveolin-2 (CAV2), CD10 (MME), CD36 (FAT/SCARB3), CD90 (Thy-1), CD91 (low density lipoprotein receptor-related protein 1, LRP1), CD146 (cell surface glycoprotein MUC18, MCAM), CD166 (activated leukocyte cell adhesion molecule, ALCAM), CLH-22 (clathrin heavy chain chromosome 22), DPT (dermatopontin), FABP4 (fatty acid binding protein 4), GLUT4 (glucose transporter 4, SLC2A4), NPR1 (Natriuretic peptide receptor A), SLC27A1 (FATP1), and SLC27A2 (FATP2). Other specific (positive) markers of adipose tissue include adiponectin, BMP7, BMP8b, CIDEC, FGF 17, FGF 19, leptin, LPL, MetAP2, NR1H3 (LXRA), perilipin 1, perilipin 2, perilipin 3, PPARG, RBP4, and resistin.

Figure 10:
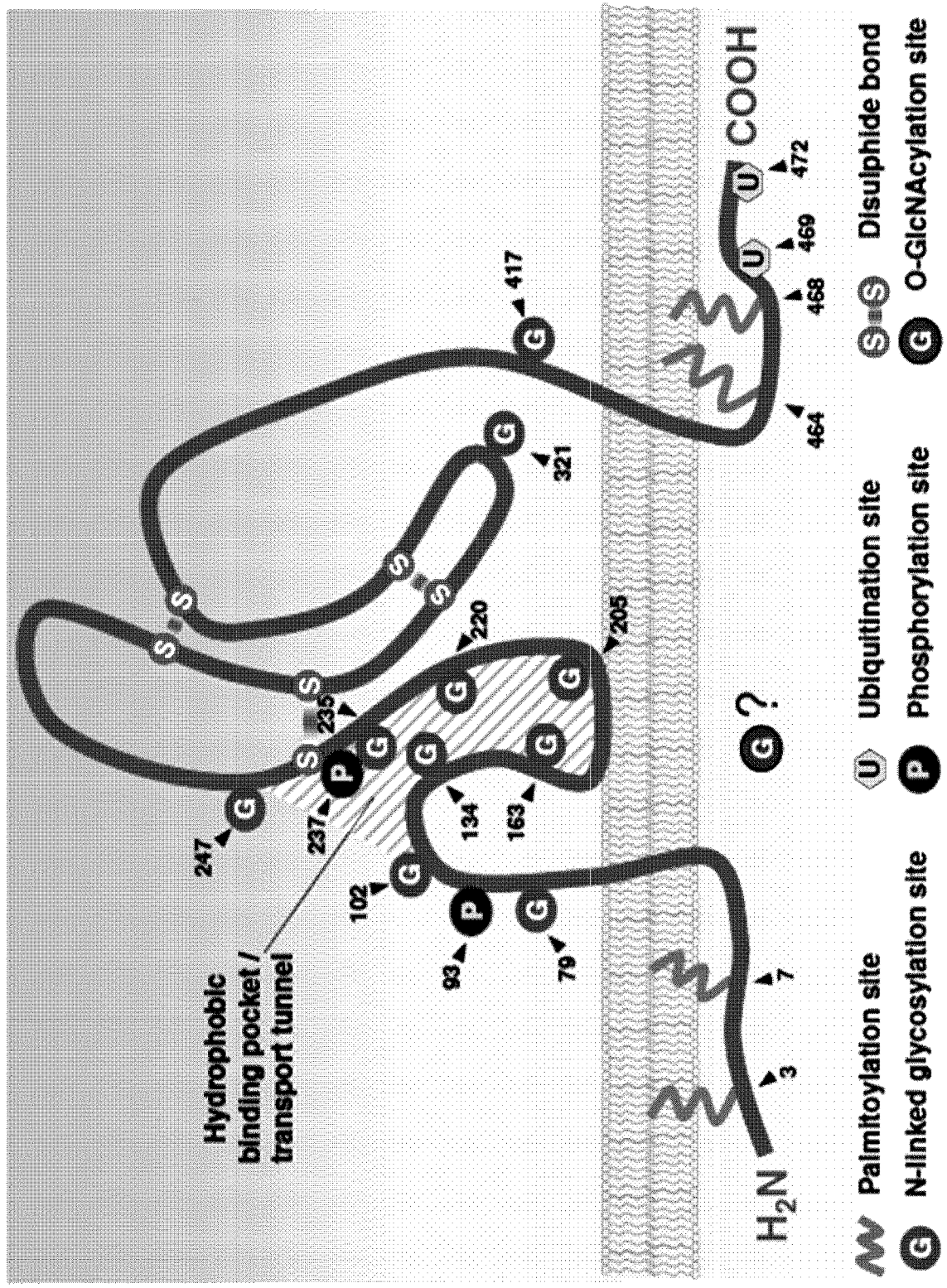
FIG. 10 shows the structure of the Fatty Acid Transporter (FAT/CD36/SCARB3) [11].

Cell surface proteins cycle intra-cellularly to some extent, and many surface receptors and transporters are actively internalized in response to ligand binding. For example, the Fatty Acid Transporter (FAT, a.k.a CD36 or SCARB3) is an integral membrane glycoprotein made of a single chain of 472 amino acids (53 kDa) that has a hairpin membrane topology with two transmembrane spanning regions, with both the $NH_2$ and COOH termini as short segments in the cellular cytoplasm [18-20], (FIG. 10)[20]:

FAT cycles between the adipocyte membrane and intra-cellular compartments (endosomes). Therefore, molecules that bind to adipocyte cell surface receptors/transporters may be exploited for the delivery of a variety of thermogenic modulators into cells.

In some embodiments, compositions may comprise targeting elements which selectively bind one or more the above-identified markers, thus enhancing the selective delivery of thermogenic modulators to adipocytes in order to enhance thermogenesis. Knowledge of the cell surface markers allows for their isolation by Flow Cytometry Cell Sorting (FACS) for subsequent screening and selection of targeting agents.

Thermogenic modulators may also be delivered in lipid nanoparticle (LNP) formulations. In some embodiments, LNP delivery of oligonucleotides involves encapsulation of the oligonucleotides inside a nanoparticle made of three components: structural lipids that form the lipid bilayer and maintain its rigidity; a cationic lipid to promote the incorporation of the negatively charged oligonucleotides into the particle and to facilitate escape from the endosomal pathway after cell internalization; and a "shield", often polyethylene glycol, to increase circulation time and minimize plasma protein binding [21]. An LNP-formulated oligonucleotide can be administered intravenously and, when it is, most of the drug ends up in the liver. Consequently, the technology has primarily been applied to life-threatening hepatic diseases (cancer and hepatitis). However, the inventors have discovered that LNPs can be used to deliver thermogenic regulators to adipocytes by injection directly into adipose tissue.

V. Example

Figure 4:
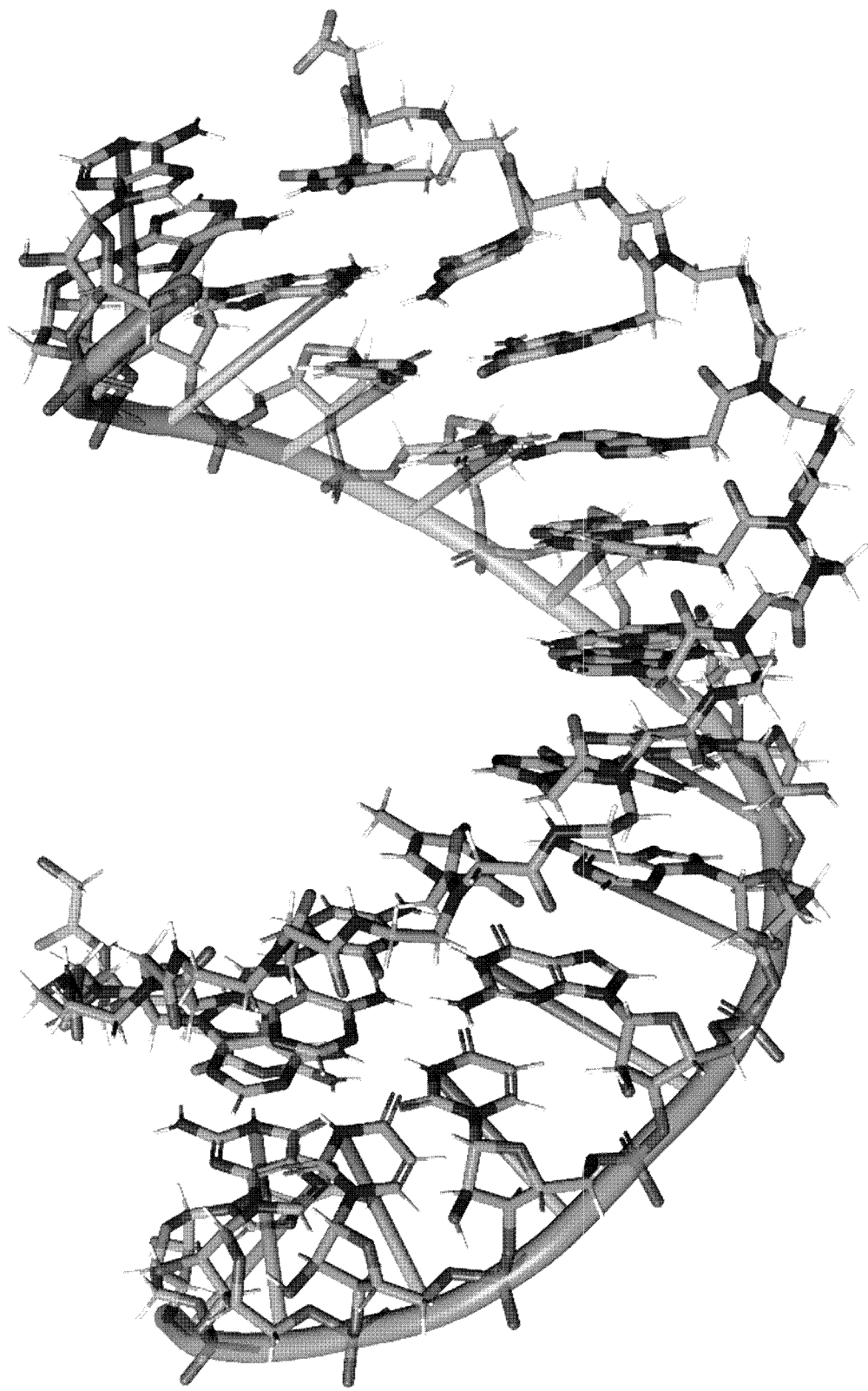
FIG. 4 shows the 3-D model of an 8-mer miR-22-3p antagomir interacting with the seed region of the human miR-22-3p target using Molecular Dynamics simulation programs.
Figure 5:
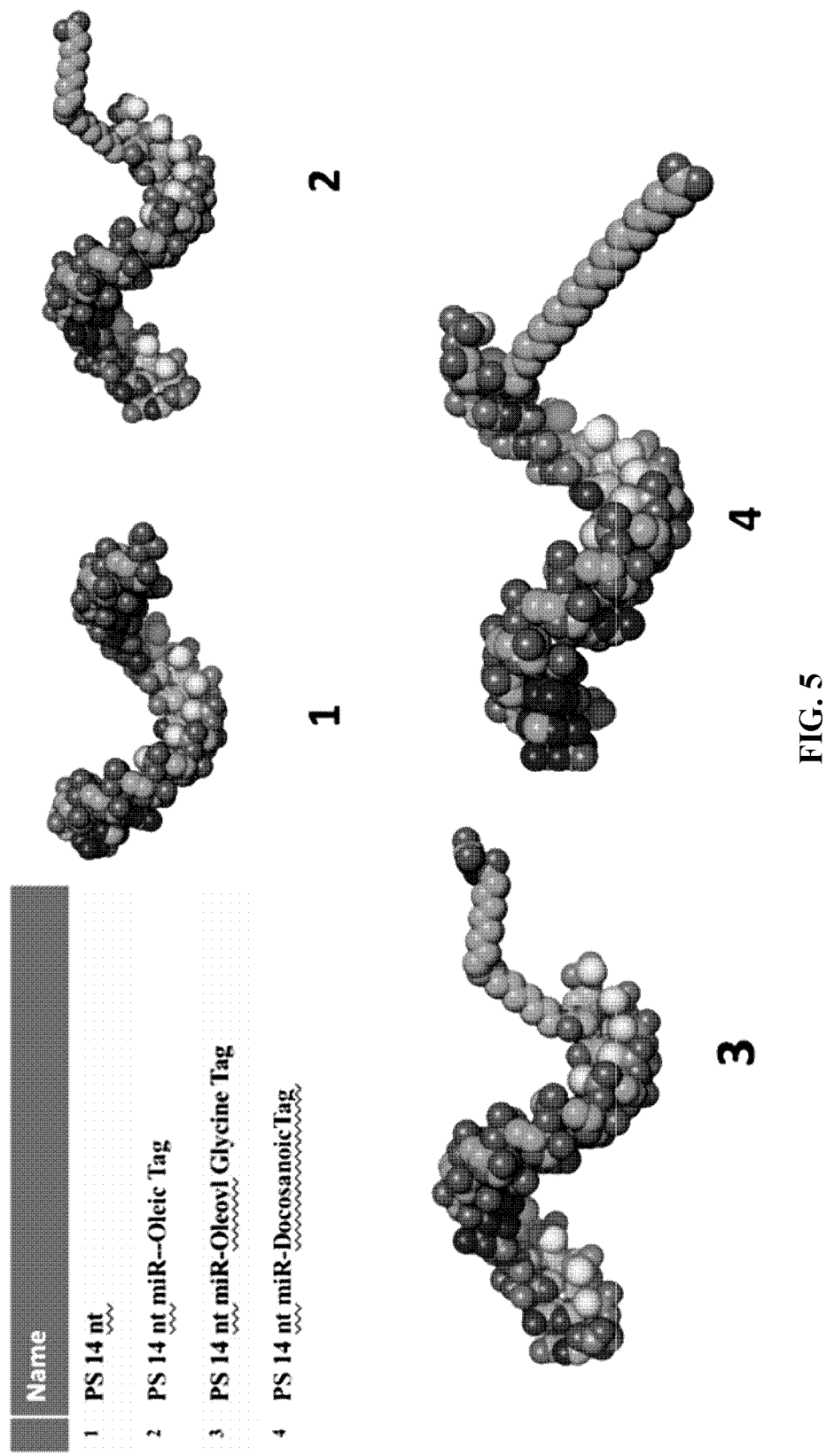
FIG. 5 shows 3-D models of the indicated AdipomiRs generated using the PyMOL program.
Figure 6:
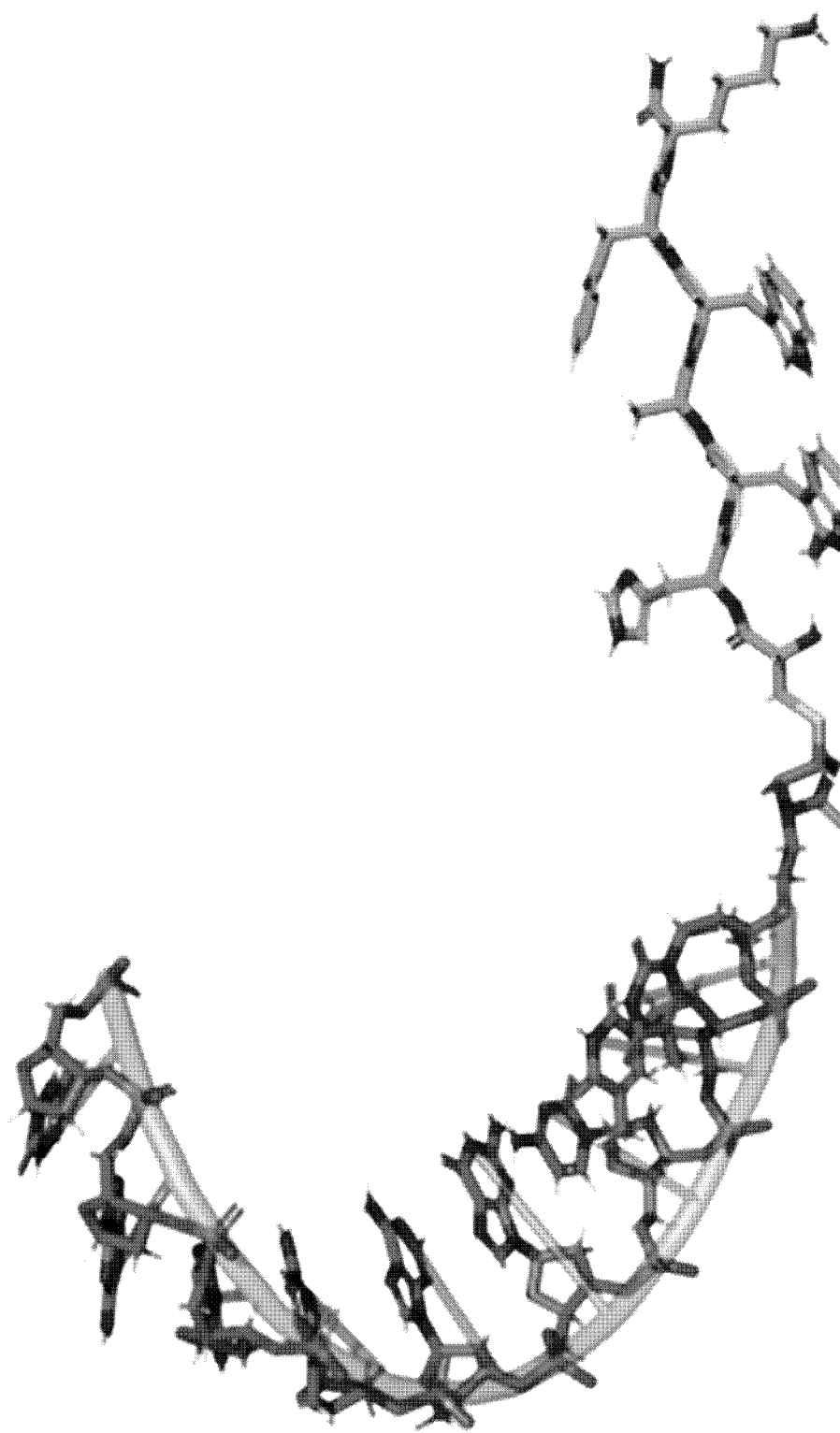
FIG. 6 shows the 3-D model of a 12-mer miR-22-3p antagomir with a peptide nucleic acid backbone targeting the seed region of the human miR-22-3p and linked to Hexarelin via a disulfide bond generated using Molecular Dynamics simulation programs.

A. Example 1: Single-Stranded miRNA (Ss-miRNA) Analogs with Modified Structure and Length Considering the critical role of the seed region (bases 2-8) and the required interaction with Ago2 protein for the ss-miRNAs to work, ss-miRNA analogs of varying length that include the following chemical modifications will be made: 5'-(E)-vinylphosphonate protection (5'-VP), phosphorothioate (PS) backbone, 2'F, 2'-O-Me and 2'-O-MOE modifications, 5-methyl cytosine modifications, introduction of a "pyrimidine cassette," and introduction of a "DNA gap" to make a "gapmer." These molecules, either alone ("naked") or combined to a lipid tag (e.g. cholesterol or fatty acid of increasing length) or a short peptide tag (e.g. Hexarelin), will be tested in a model of primary cultures of human subcutaneous adipocytes, the ultimate targets for an anti-obesity drug, as illustrated in FIG. 4-6.

B. Example 2: Fatty Acid/miRNA Conjugates

An extensive "Omic" profiling of mature human subcutaneous adipocytes and their exosomes was performed. The inventors observed a high level of expression of Fatty Acid Translocase (FAT, a.k.a. scavenger receptor B3 or CD36), which is an integral cell membrane transporter involved in fatty acid uptake into adipocytes [19, 22-25]. It is expected that combining a ss-miRNA analog to a fatty acid that is naturally transported by FAT will facilitate targeted delivery of such ss-miRNA analog to mature adipocytes. This will be shown by synthesizing and validating a series of miRNA analogs that are covalently attached to fatty acids to facilitate preferential targeting of and transport by adipocyte FAT. These miRNA analogs are referred to herein as AdipomiRs (Adipocyte-targeting miRNAs).

AdipomiR Synthesis: Fatty acids have been used as chemical permeation enhancers (CPE) for various drugs, including oligonucleotides [26] [27]. Conjugates made of single stranded miRNA analogs conjugated to fatty acids (AdipomiRs) will be synthesized. Fatty acids of varying lengths will be attached at the 3' of miRNA analogs. Fluorescently labeled and scrambled miRNA AdipomiRs will also synthesized. Table 2 below categorizes fatty acids by length:

TABLE 2

Categorization of Fatty Acids by Length

| | |
|---|---|
| Medium Chain Fatty Acids | C10:0 Decanoic Acid |
| | C12:0 Dodecanoic Acid |
| Long Chain Fatty Acids | C16:0 Palmitic Acid |
| | C18:0 Stearic Acid |
| | C18:1 Oleic Acid |
| Very Long Chain Fatty Acids | C22:0 Docosanoic acid |
| | C32:6 Dotriacontahexaenoic Acid |
| Omega-3 Fatty Acids | C22:6 Docosahexaenoic acid |

In Silico Modeling of AdipomiRs: The open-source model visualization PyMOL program was used to produce 3D images of single stranded miRNA analogs conjugated to fatty acids. FIG. 5 shows the 3D model of four AdipomiRs.

In vitro validation of AdipomiRs targeted delivery of functional miRNAs: The ability of the AdipomiRs to target and deliver ss-miRNA analogs to adipocytes was evaluated in a model of primary cultures of human subcutaneous adipocytes. The first experimental step was to confirm that fatty acids are efficiently transported into human mature adipocytes, using the inventor's in vitro protocol of primary cultures of human subcutaneous adipocytes. To test this, fatty acids such as palmitic and hexadecanoic acids were labeled with a green fluorescent probe and incubated with cultured adipocytes. Examination of the adipocytes by fluorescence microscopy showed that the labeled fatty acids were very efficiently transported by human adipocytes in primary culture.

For the next step to confirm the adipocyte delivery of the AdipomiRs, human adipocytes will be incubated with various concentrations (25 to 100 nM) of AdipomiRs. At several time points from 1 to 48 hours, cells will be collected for confocal microscopy, high content imaging, and qRT-PCR of miRNA analogs and target genes to validate adipocyte uptake of functional thermogenic miRNA analogs. To validate that AdipomiR binding and internalization is FAT-dependent, cells will be pre-treated with sulfo-N-succinimidyl oleate (SSO, a known inhibitor of FAT). These AdipomiRs will also be tested in human pre-adipocytes, macrophages and hepatocytes to assess cellular uptake selectivity.

In vivo AdipomiR biodistribution and efficacy: AdipomiRs showing in vitro enhanced transport of functional thermogenic miRNA analogs into mature human adipocytes will be further tested in vivo. Using diet-induced obese (DIO) C57B1/6J mice, selected AdipomiRs will be tested for tissue biodistribution and therapeutic efficacy in studies conducted at UT Austin Animal Resources Center under IACUC-approved biodistribution and efficacy protocols. Toxicity will be monitored by twice daily monitoring of animals. Biodistribution of AdipomiRs to vital tissues and organs will be assessed by harvesting them on Day 7 after subcutaneous injections of the AdipomiRs in the inguinal fat pad on Days 0, 2, and 4 for histology staining and qRT-PCR of miRNA analogs and target genes. "Naked" miRNA analogs (15 mg/kg) will be used as controls.

The ability of AdipomiRs to induce WAT to BAT thermogenic browning will be determined in DIO mice. At the start of the 8-week study, DIO mice will be maintained on a normal chow or 60% high fat diet and treated with subcutaneous injections of AdipomiRs into the inguinal fat pad on day 0, 2, and 4 of the first week, followed with once weekly injections for the remainder of the study. Mice will undergo body composition analysis by NMR at weeks 1 and 8 of treatment Lipid parameters and insulin sensitivity will be assessed. Post-treatment, animals will be sacrificed with blood collected for analysis along with vital tissues and organs for histological and gene expression analyses. It is expected that the mice being administered AdipomiRs will have reduced body fat, reduced insulin sensitivity, and favorable lipid parameters. Exemplary AdipomiRs that are expected to have this activity include single-stranded miR-22 antagomirs and miR-515 agomirs conjugated to medium chain fatty acids, long chain fatty acids, or very long chain fatty acids.

C. Example 3: Hexarelin/miRNA Conjugates

Hexarelin, a chemically stable and potent Growth Hormone secretagogue (His-D-2-Me-Trp-Ala-Trp-D-Phe-Lys-NH2, Molecular Formula: $C_{47}H_{58}N_{12}O_6$, Molecular Weight: 887), has recently been shown to have beneficial effects on fat metabolism via the FAT/CD36 transporter [28, 29], resulting in fatty acid mobilization and activation of mitochondrial oxidative phosphorylation and thermogenesis. Hexarelin treatment significantly improved glucose and insulin intolerance and decreased plasma and liver triglycerides in MKR insulin-resistant mice. Furthermore, the cardioprotective effects of hexarelin are well documented [30].

It is expected that combining a ss-miRNA analog to hexarelin that is naturally transported by FAT will facilitate targeted delivery of such ss-miRNA analog to mature adipocytes. Therefore, a series of miRNA analogs that are covalently attached to hexarelin to facilitate preferential targeting to adipocyte FAT will be synthesized and evaluated. These hexarelin-conjugated miRNAs are referred to herein as HexamiRs (Hexarelin-conjugated miRNAs).

In Silico Modeling of HexamiRs: As described above, open-source Molecular Dynamics simulation programs were used to produce 3D images of single stranded miRNA analogs conjugated to Hexarelin as shown on FIG. 6.

Figure 7:
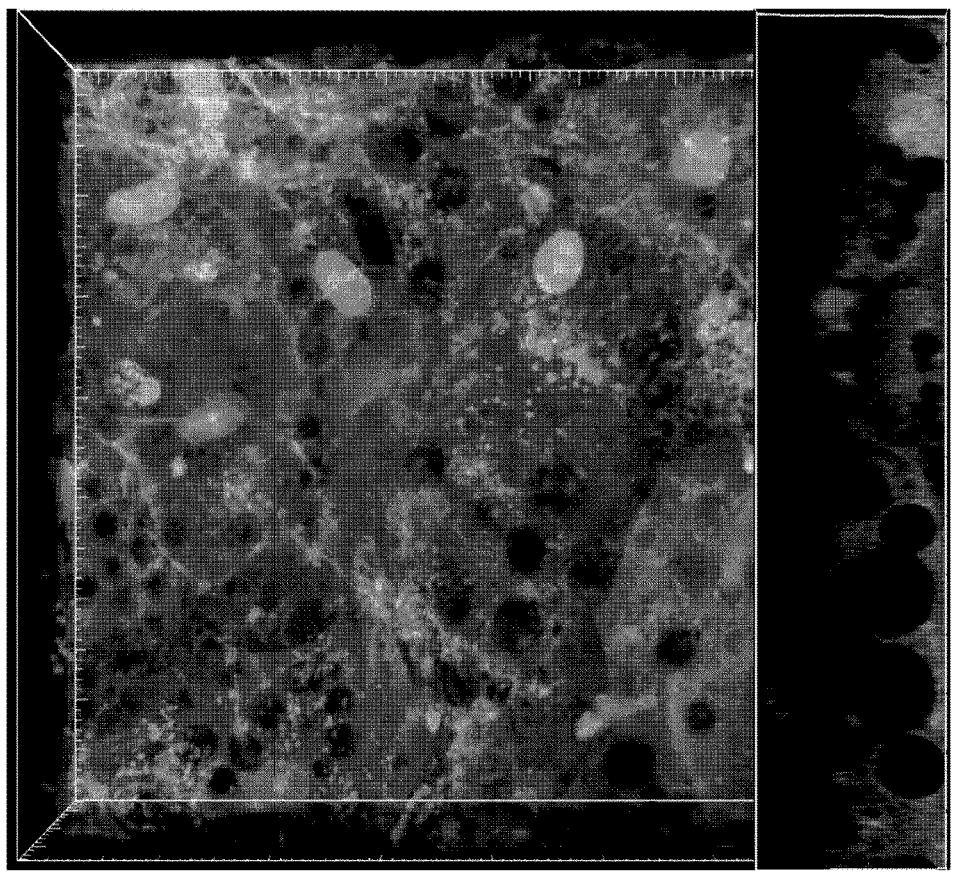
FIG. 7 shows the efficient transport of green fluorescent Hexarelin in to the cytoplasm of human adipocytes.
Figure 7:
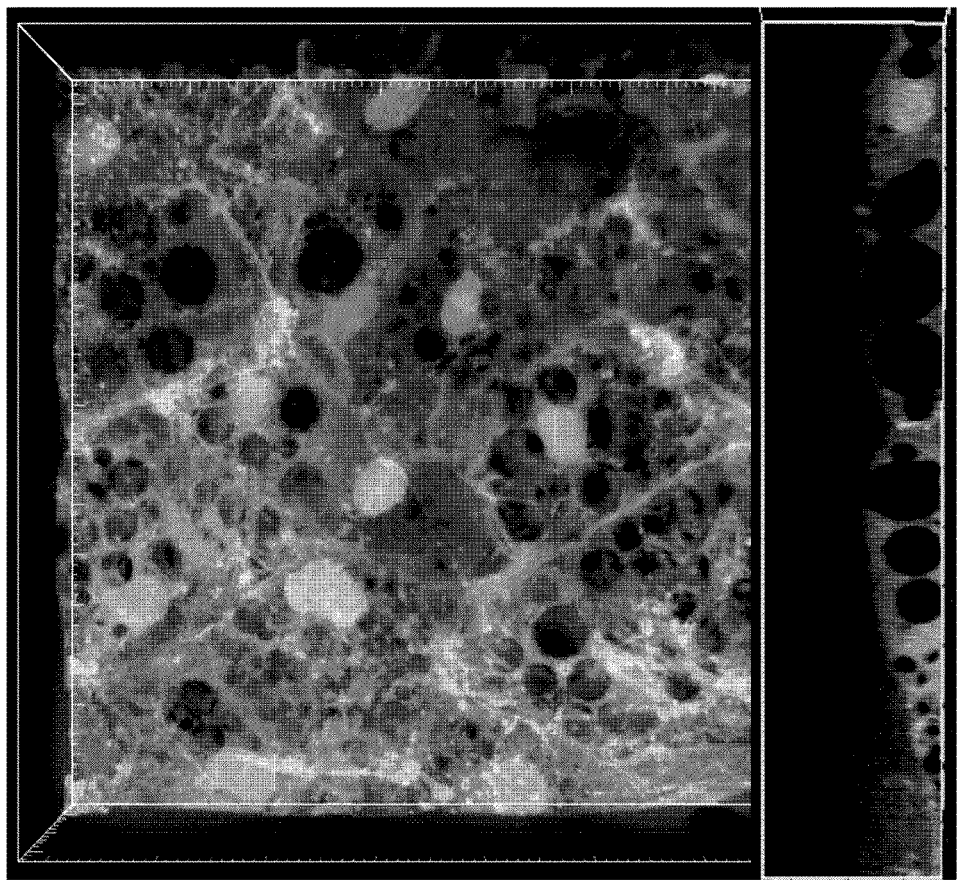

In vitro validation of HexamiRs targeted delivery of functional miRNAs: The ability of the HexamiRs to target and deliver ss-miRNA analogs to adipocytes will evaluated in a model of primary cultures of human subcutaneous adipocytes. The first experimental step was to confirm that Hexarelin is efficiently transported into human mature adipocytes, using an in vitro protocol of primary cultures of human subcutaneous adipocytes. To test this, hexarelin labeled with a green fluorescent probe was incubated with cultured adipocytes. Examination of the cultured adipocytes by fluorescence microscopy showed that hexarelin was very efficiently transported into the cytoplasm of human adipocytes as shown on FIG. 7.

The subsequent in vitro and in vivo validation steps of the HexamiRs will rely on the experiments described above for the AdipomiRs. It is expected that the mice being administered HexamiRs will have reduced body fat, reduced insulin sensitivity, and favorable lipid parameters. Exemplary HexamiRs expected to have this activity include single-stranded miR-22 antagomirs and miR-515 agomirs conjugated to His-D-2-Me-Trp-Ala-Trp-D-Phe-Lys-$NH_2$.

D. Example 4: Lipid Nanoparticles/miRNA Conjugates

Lipid nanoparticles (LNPs) have been optimized for cellular uptake and efficient endosomal escape of siRNAs after systemic administration [31-33], but have not been extensively evaluated after local delivery to adipose tissue.

Figure 8A:
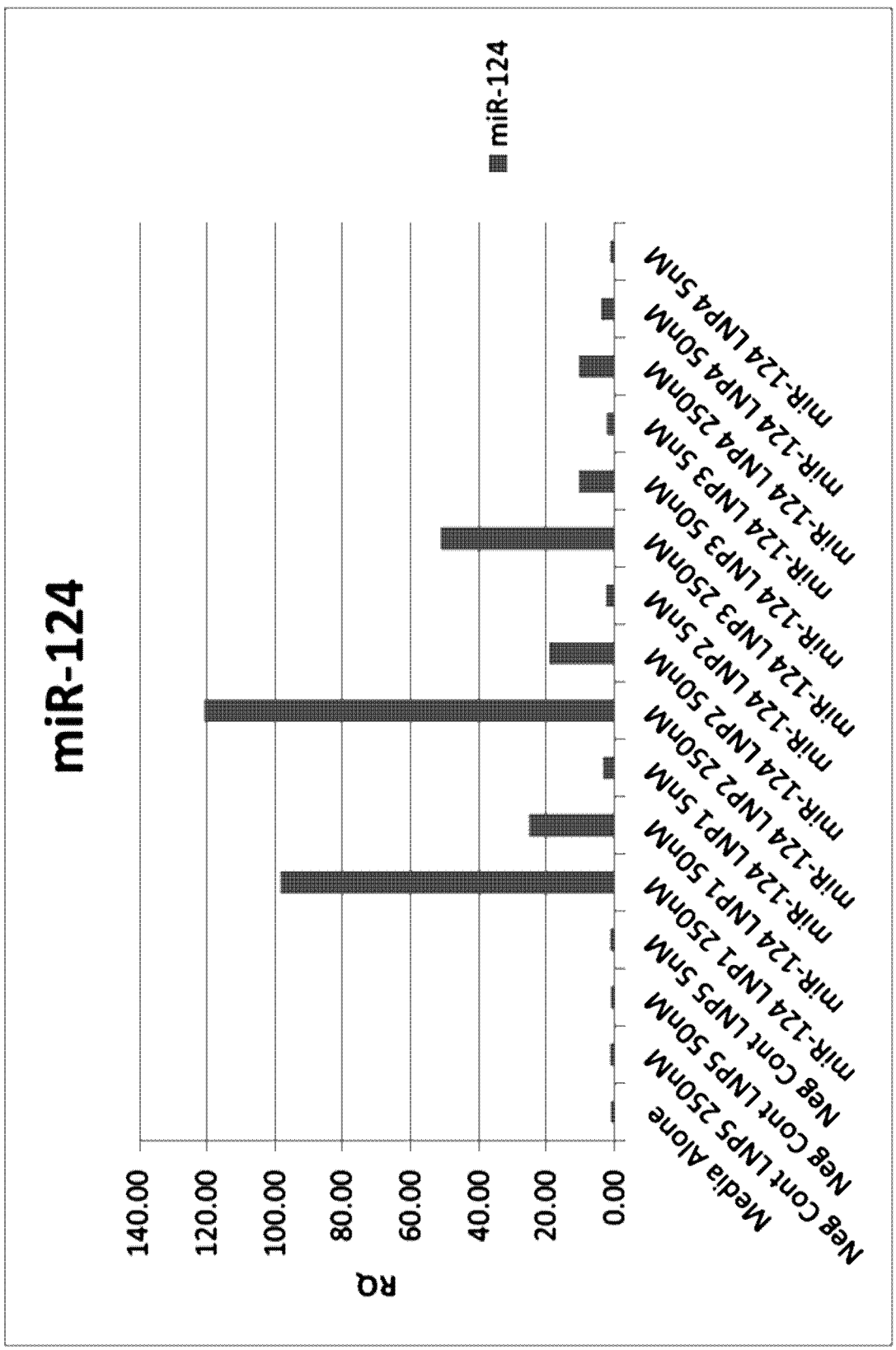
FIGS. 8A-D are graphs showing the relative abundance of the indicated RNAs, as measured by qRT-PCR in adipocytes incubated with the indicated amounts of a double stranded miR-124 in a formulation with lipid nanoparticles LNP1, LNP2, LNP3, or LNP4, as indicated. (A) relative abundance of miR-124; (B) relative abundance of let-7 mRNA; (C) relative abundance of IQGAP1 mRNA; (D) relative abundance of leptin mRNA.
Figure 8B:
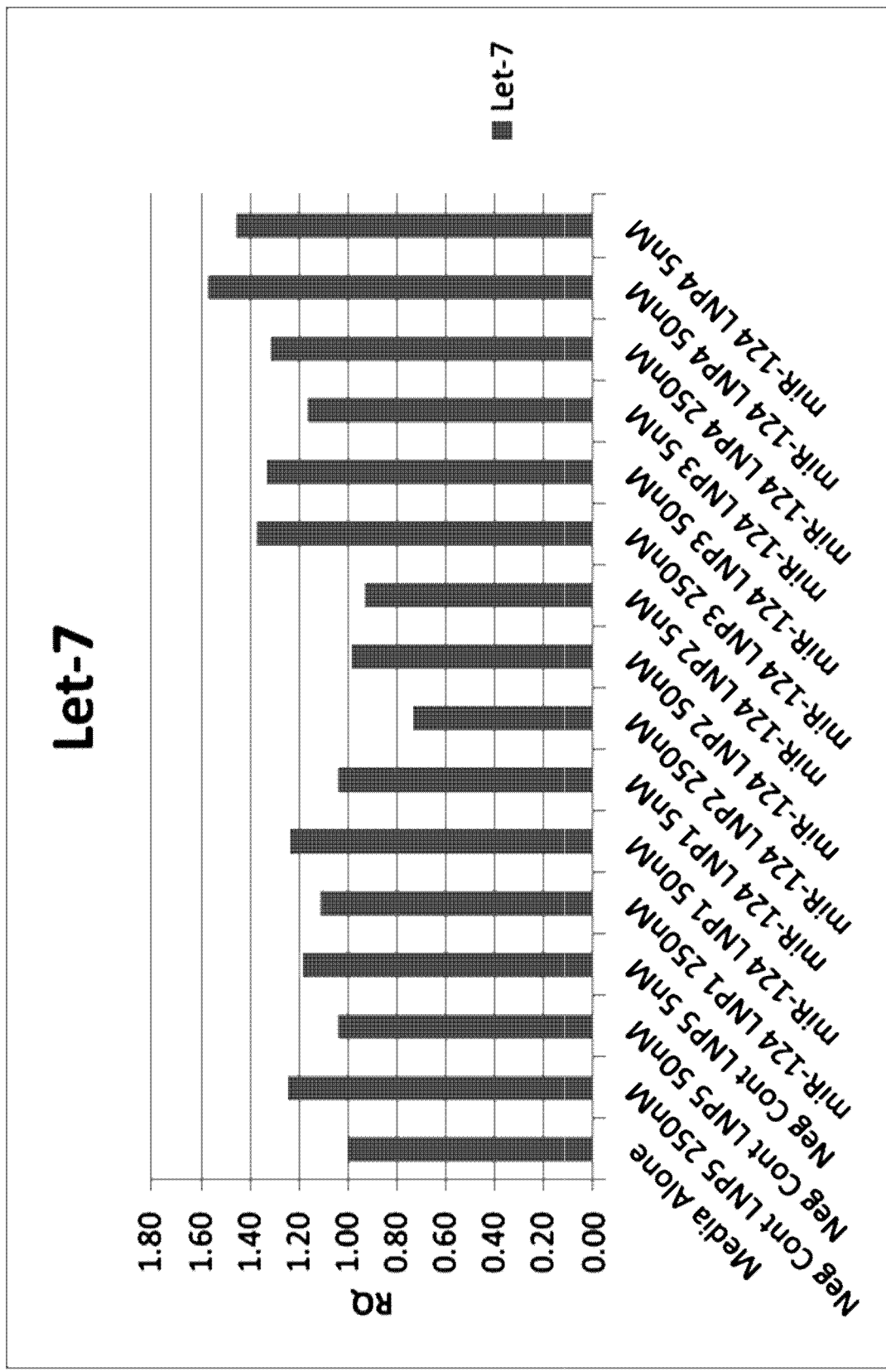
Figure 8C:
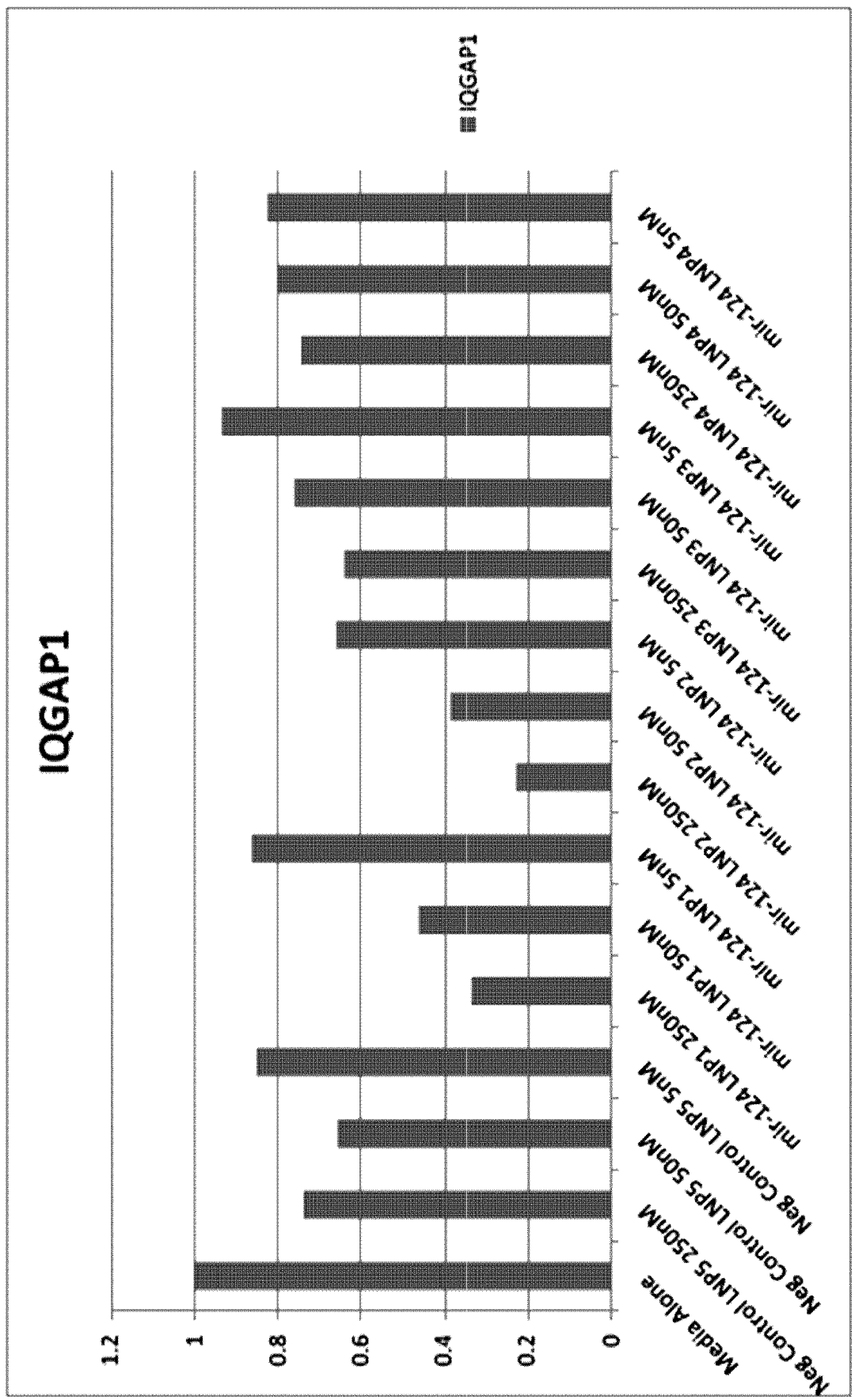
Figure 8D:
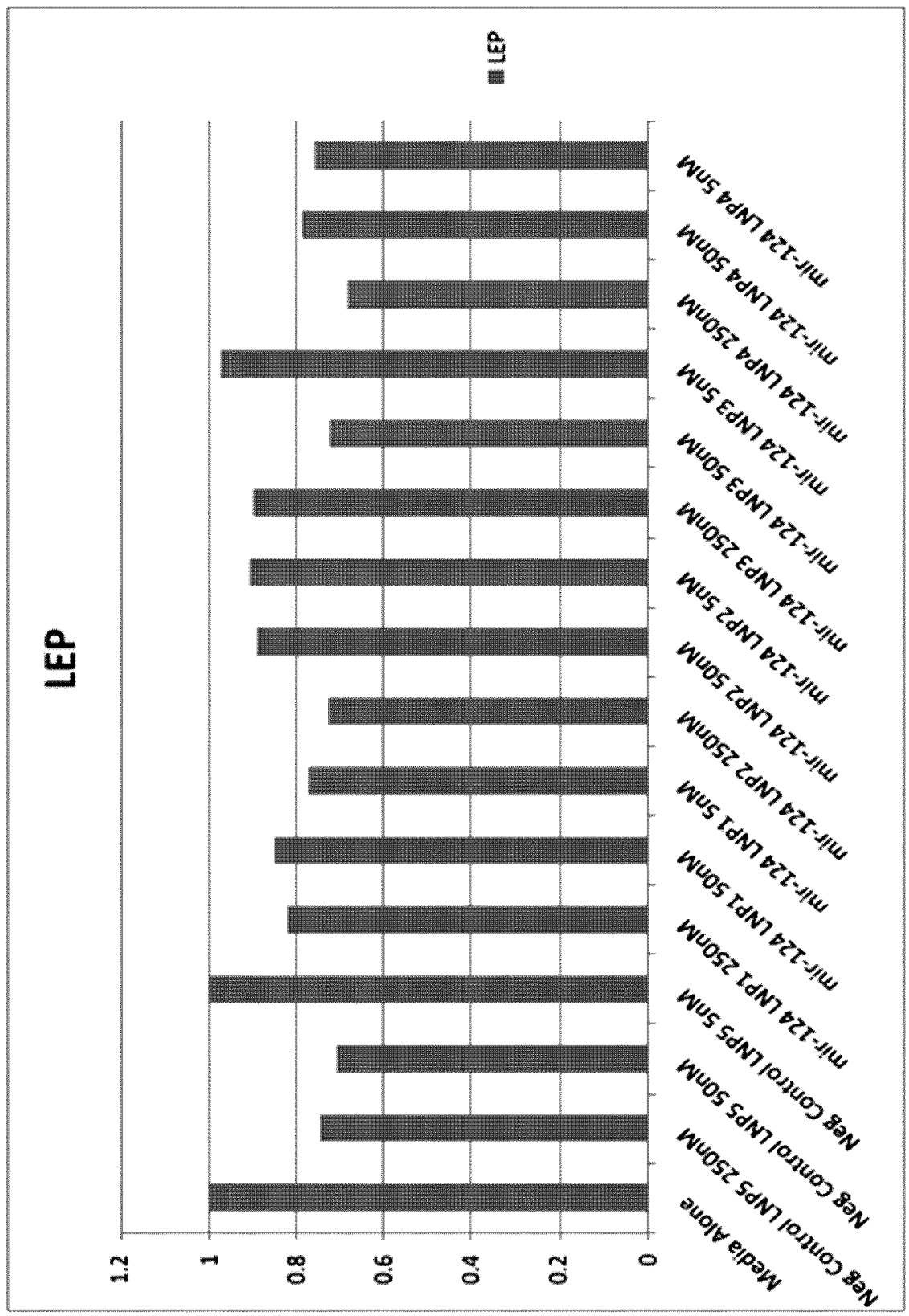

In vitro LNP delivery of a control miRNA to human adipocytes: An experiment was performed with LNPs made of structural lipids, a cationic lipid, and PEG. Four different LNP formulations were used: LNP1, LNP2, LNP3, and LNP4. Mature human adipocytes in primary culture were transfected with a negative control (empty LNPs) or LNPs loaded with varying amounts (5 to 250 nM) of a double stranded miR-124 (a miRNA that is not expressed in adipocytes). Two days later, the amount of miR-124 introduced into the adipocytes and the down-regulation of target mRNAs were measured by qRT-PCR As shown in FIG. 8A, miR-124 was detected in the adipocytes in a dose-dependent fashion (RQ up to 121-fold) whereas the expression of 2 control miRNAs (let-7 (FIG. 8B) and miR-143 (not shown)) was not modified. FIG. 8A also shows that LNP1 and LNP2 provided the most efficient delivery of miRNA, LNP3 provided an intermediate level of efficiency, and LNP4 was relatively inefficient. The expression of 3 target genes of miR-124 (CD164 (not shown), IQGAP1 (FIG. 8C), VAMP3) was knocked down in a dose-dependent fashion whereas the expression of 2 control genes (FABP4 (not shown) and leptin (FIG. 8D)) was not modified.

Figure 9:
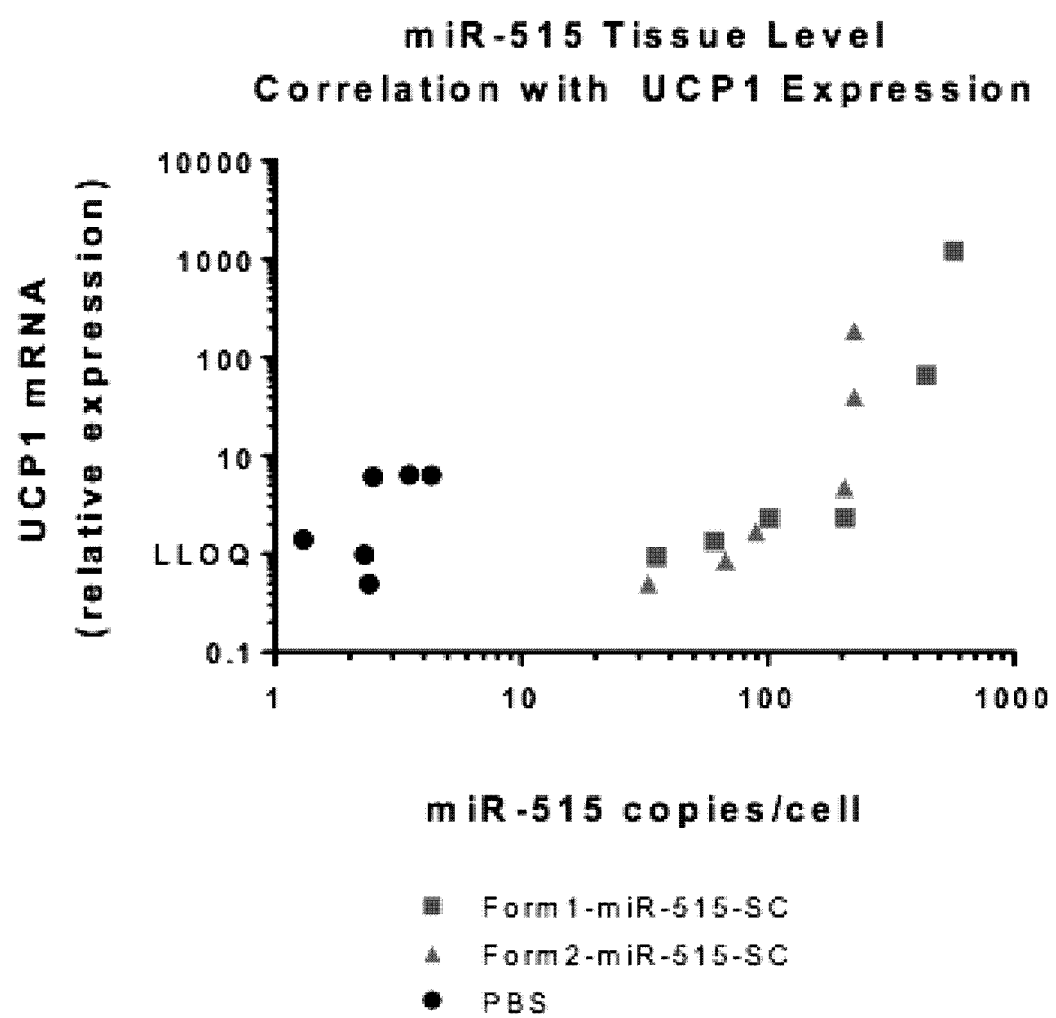
FIG. 9 is a graph showing relative expression of UCP1 mRNA correlated to the amount of miR-515 copies per cell in mouse tissue after subcutaneous injection in mice.

In vivo LNP delivery of a thermogenic miRNA to murine adipocytes: The two LNPs that most efficiently delivered a control double stranded miRNA mimic (miR-124) to human adipocytes in culture (LNP1 and LNP2), were tested in mice. The biodistribution across various organs and tissues of these two LNPs administered SC or IV, carrying either the control miR-124 or a thermogenic double stranded human miR-515-3p mimic (Dharmacon), was tested in obese C57BL/6J male mice placed on a high fat diet After either a single subcutaneous injection on Day 2 or three intravenous injections on Days 0, 1 and 2, organs and tissues were collected on Day 4. As expected, intravenous injections of the LNPs led to accumulation of the miR-515 mimic mostly into the liver and kidneys with no or little uptake by various adipose tissues. However, after single subcutaneous injection, the LNPs provided delivery of the thermogenic miRNA mimic into the left inguinal fat pad (site of the subcutaneous injection). When enough copies of the miR-515 mimic were delivered into the inguinal fat pad (>100 miRNA copies per cell), a significant dose-dependent increase of UCP1 mRNA expression was observed (FIG. 9) indicates LNP1 and Form 2 indicates LNP2). Surprisingly, after single subcutaneous injection one of the nanoparticles (LNP2) also delivered the miR-515 mimic to the lungs, kidneys, and quadriceps muscle. In summary, this study provided proof of concept of intracellular delivery of an LNP-carried double stranded miRNA mimic into mouse subcutaneous adipose tissue that translates into upregulation of UCP1 gene expression once a small amount of such miRNA is present inside the tissue. However, PEGylated LNPs may not be appropriate for delivery of miRNA in humans because of their biodistribution profile. Furthermore, cationic lipids can induce damage to cell membranes. Therefore, additional LNPs were developed.

SDC Liposome formulations: Sphingomyelin is the most abundant phospholipid (40%) of the human adipocyte membrane. Sphingomyelin combines with cholesterol to form lipid rafts that are involved in many cell processes, such as membrane sorting and trafficking, signal transduction, and cell polarization [34, 35]. Sphingomyelin/cholesterol liposomes have greater stability than DSPC/cholesterol liposomes and can deliver more efficiently entrapped drugs [36]. A variety of liposomes of differing compositions were characterized. The best-performing Liposome candidate contained sphingomyelin, 1,2-dimyristoyl-sn-glycero-3-phosphocholine (DMPC), and cholesterol at a 40:40:20% weight to weight ratio. These "SDC" liposomes are well-characterized with a peak mean diameter of 140 nm, a polydispersity index (PDI) of <0.01, and a Zeta potential of +2.32 mV with no significant changes during storage over 3 months at 4° C.

Complexation of SDC Liposomes with thermogenic miRNAs (LipomiRs): Addition of miR-515 agomir to purified SDC liposomes slightly increased their size to ~147 nm with PDI of <0.032 and reduced their zeta potential from +2.32 mV to −55.7 mV, indicative of miRNAs surface association. Using high content fluorescence imaging, these SDC liposome miRNA complexes (LipomiRs) showed efficient delivery of fluorescent and functional miRNAs into adipocytes.

Uptake of miRNA was visually confirmed by microscopy along with a dose dependent induction of UCP1 seen by qRT-PCR analysis. UCP1 upregulation was analogous to positive control of free miRNA delivered by a DharmaFect transfection reagent

E. Example 5: Fatty Acid Conjugated miRNAs Anchoring to SDC Liposomes (AdipoLipomiRs)

Fatty acid conjugated miRNAs (AdipomiRs) may be able help anchor thermogenic miRNA analogs onto the SDC liposome membrane. Two approaches can be employed. Firstly, the AdipomiRs can be introduced during lipid film preparation/hydration, resulting in improved internal and external anchoring to SDC liposomes. Secondly, SDC liposomes can be prepared beforehand followed by incubation with fatty acid conjugated miRNAs for surface membrane anchoring via lipophilic interactions. The first approach suffers from significant loss of conjugated miRNA during the liposome sizing extrusion process but benefits from higher internal encapsulation of miRNAs within the liposome lumen, thereby affording additional protection and delivery capacity during systemic transport. As a complementary approach, encapsulation of minimally modified miRNAs conjugated to fatty acids for membrane anchoring during lipid hydration will be attempted as a means of reducing costs and complexity. Free or fatty acid-conjugated miRNA analogs will be added either during or after SDC liposome formation to compare loading efficacy. LipomiR size and charge will be used to assess exterior loading of miRNAs while total miRNA retention levels can be assayed by UV-vis spectroscopy and miRNA extraction using Triton X-100 followed by RiboGreen fluorescence quantification. Ionic competition using dextran sulfate will be used to evaluate fatty acid anchoring of miRNAs to the liposome surface. To evaluate miRNA stability, miRNA-loaded SDC liposomes will be incubated in the presence of human serum. At various time points, miRNAs will be evaluated for degradation by HPLC. While miRNAs will complex with SDC liposomes due to the presence of the weakly cationic DMPC, the conjugation of fatty acid may be a key factor in improving long term stability within assembled LipomiRs. Furthermore, it may allow for removal of DMPC entirely, thereby further simplifying scale-up manufacturability and safety. Additionally, a soluble fluorescent marker can be packaged internally within these liposomes during preparation to reveal a two-tone fluorescent nanoparticle with peripheral rim vs. luminal staining pattern.

F. Example 6: Other Targeting Formulations

In addition to using fatty acids to facilitate the targeted delivery of miRNA analogs to mature human adipocytes, such miRNAs can also by delivered to adipocytes by targeting adipocyte membrane proteins, such as receptors and transporters. The inventors have discovered through "omics" profiling that the following proteins are expressed in high quantities specifically in mature adipocytes: fatty acid translocase (FAT/CD36/SCARB3 NCBI gene ID 948), Aquaporin 7 (AQP7, NCBI gene ID 364), Perilipin 1 (PLIN1, NCBI gene ID 5346), and Perilipin 2 (PLIN2, NCBI gene ID 123). FAT can be targeted, for example, with a VHH single domain antibody (15 kDa) [37] or other specific antibodies, Trombospondin-1 peptide (GVITRIR) [38], or Hexarelin peptide [29]. The inventors have successfully performed experiments showing antibody staining of adipocyte cell membranes with anti-FAT antibodies and confirming the high density of FAT expression at the level of adipocyte cell membrane. AQP7, PLIN1, and PLIN2 can also be targeted with specific antibodies.

REFERENCES

1. Younossi, Z., et al., Global burden of NAFLD and NASH: trends, predictions, risk factors and prevention. Nat Rev Gastroenterol Hepatol, 2018. 15(1): p. 11-20.
2. Hanson, A., D. Wilhelmsen, and J. K. DiStefano, The Role of Long Non-Coding RNAs (lncRNAs) in the Development and Progression of Fibrosis Associated with Non-alcoholic Fatty Liver Disease (NAFLD). Noncoding RNA, 2018. 4(3).

3. Sarwar, R., N. Pierce, and S. Koppe, Obesity and nonalcoholic fatty liver disease: current perspectives. Diabetes Metab Syndr Obes, 2018. 11: p. 533-542.
4. Buzzetti, E., M. Pinzani, and E. A. Tsochatzis, The multiple-hit pathogenesis of non-alcoholic fatty liver disease (NAFLD). Metabolism, 2016. 65(8): p. 1038-48.
5. Li, Z. and T. M. Rana, Therapeutic targeting of microRNAs: current status and future challenges. Nat Rev Drug Discov, 2014. 13(8): p. 622-38.
6. van Rooij, E. and S. Kauppinen, Development of microRNA therapeutics is coming of age. EMBO Mol Med, 2014. 6(7): p. 851-64.
7 Zhang, Y., Z. Wang, and R. A. Gemeinhart, Progress in microRNA delivery. J Control Release, 2013. 172(3): p. 962-74.
8. Wittrup, A. and J. Lieberman, Knocking down disease: a progress report on siRNA therapeutics. Nat Rev Genet, 2015. 16(9): p. 543-52.
9. Alexander, R., H. Lodish, and L. Sun, MicroRNAs in adipogenesis and as therapeutic targets for obesity. Expert opinion on therapeutic targets, 2011. 15: p. 623-36.
10. Yu, D., et al., Single-stranded RNAs use RNAi to potently and allele-selectively inhibit mutant huntingtin expression. Cell, 2012. 150(5): p. 895-908.
11. Glatz, J. F., J. J. Luiken, and A. Bonen, Membrane fatty acid transporters as regulators of lipid metabolism: implications for metabolic disease. Physiol Rev, 2010. 90(1): p. 367-417.
12. Inui, M., G. Martello, and S. Piccolo, MicroRNA control of signal transduction. Nat Rev Mol Cell Biol, 2010. 11: p. 252-63.
13. Ha, M. and V. N. Kim, Regulation of microRNA biogenesis. Nat Rev Mol Cell Biol, 2014. 15(8): p. 509-24.
14. Matsui, M., T. P. Prakash, and D. R. Corey, Argonaute 2-dependent Regulation of Gene Expression by Single-stranded miRNA Mimics. Mol Ther, 2016. 24(5): p. 946-55.
15. Chorn, G., et al., Single-stranded microRNA mimics. RNA, 2012. 18(10): p. 1796-804.
16. Lima, W. F., et al., Single-stranded siRNAs activate RNAi in animals. Cell, 2012. 150(5): p. 883-94.
17. Hu, J., et al., Exploring the effect of sequence length and composition on allele-selective inhibition of human huntingtin expression by single-stranded silencing RNAs. Nucleic Acid Ther, 2014. 24(3): p. 199-209.
18. Glatz, J. F. and J. J. Luiken, From fat to FAT (CD36/SCARB3): Understanding the regulation of cellular fatty acid uptake. Biochimie, 2017. 136: p. 21-26.
19. Zhou, D., et al., CD36 level and trafficking are determinants of lipolysis in adipocytes. FASEB J, 2012. 26(11): p. 4733-42.
20. Luiken, J. J., et al., Post-translational modifications of CD36 (SCARB3): Implications for regulation of myocellular fatty acid uptake. Biochim Biophys Acta, 2016. 1862(12): p. 2253-2258.
21. Zatsepin, T. S., Y. V. Kotelevtsev, and V. Koteliansky, Lipid nanoparticles for targeted siRNA delivery—going from bench to bedside. Int J Nanomedicine, 2016. 11: p. 3077-86.
22. Febbraio, M., D. P. Hajjar, and R. L. Silverstein, CD36: a class B scavenger receptor involved in angiogenesis, atherosclerosis, inflammation, and lipid metabolism. The Journal of clinical investigation, 2001. 108(6): p. 785-91.
23. Pohl, J., et al., FAT/CD36-mediated long-chain fatty acid uptake in adipocytes requires plasma membrane rafts. Molecular biology of the cell, 2005. 16(1): p. 24-31.
24. Nickerson, J. G., et al., Greater transport efficiencies of the membrane fatty acid transporters FAT/CD36 and FATP4 compared with FABPpm and FATP1 and differential effects on fatty acid esterification and oxidation in rat skeletal muscle. J Biol Chem, 2009. 284(24): p. 16522-30.
25. Coburn, C. T., et al., Defective uptake and utilization of long chain fatty acids in muscle and adipose tissues of CD36 knockout mice. J Biol Chem, 2000. 275(42): p. 32523-9.
26. Hardee, G. E., Oral delivery of nucleic acid-based therapeutics. Ther Deliv, 2012. 3(2): p. 143-5.
27. Maher, S., et al., Safety and efficacy of sodium caprate in promoting oral drug absorption: from in vitro to the clinic. Adv Drug Deliv Rev, 2009. 61(15): p. 1427-49.
28. Mosa, R., et al., Hexarelin, a Growth Hormone Secretagogue, Improves Lipid Metabolic Aberrations in Nonobese Insulin-Resistant Male MKR Mice. Endocrinology, 2017. 158(10): p. 3174-3187.
29. Rodrigue-Way, A., et al., A growth hormone-releasing peptide promotes mitochondrial biogenesis and a fat burning-like phenotype through scavenger receptor CD36 in white adipocytes. Endocrinology, 2007. 148(3): p. 1009-18.
30. Mao, Y., T. Tokudome, and I. Kishimoto, The cardiovascular action of hexarelin. J Geriatr Cardiol, 2014. 11(3): p. 253-8.
31. Yu, B., et al., Insight into Mechanisms of Cellular Uptake of Lipid Nanoparticles and Intracellular Release of Small RNAs. Pharm Res, 2014.
32. Dong, Y., et al., Lipopeptide nanoparticles for potent and selective siRNA delivery in rodents and nonhuman primates. Proc Natl Acad Sci USA, 2014. 111(11): p. 3955-60.
33. Dahlman, J. E., et al., In vivo endothelial siRNA delivery using polymeric nanoparticles with low molecular weight. Nat Nanotechnol, 2014.
34. Milhas, D., C. J. Clarke, and Y. A. Hannun, Sphingomyelin metabolism at the plasma membrane: implications for bioactive sphingolipids. FEBS Lett, 2010. 584(9): p. 1887-94.
35. Lajoie, P., et al., Lattices, rafts, and scaffolds: domain regulation of receptor signaling at the plasma membrane. J Cell Biol, 2009. 185(3): p. 381-5.
36. Webb, M. S., et al., Sphingomyelin-cholesterol liposomes significantly enhance the pharmacokinetic and therapeutic properties of vincristine in murine and human tumour models. Br J Cancer, 1995. 72(4): p. 896-904.
37. Berre, S., et al., CD36-specific antibodies block release of HIV-1 from infected primary macrophages and its transmission to T cells. J Exp Med, 2013. 210(12): p. 2523-38.
38. Kong, P., et al., Thrombospondin-1 regulates adiposity and metabolic dysfunction in diet-induced obesity enhancing adipose inflammation and stimulating adipocyte proliferation. Am J Physiol Endocrinol Metab, 2013. 305(3): p. E439-50.

The invention claimed is:
1. An adipocyte-targeting composition comprising:
(a) a therapeutic agent capable of modulating lipid oxidation and/or thermogenic regulation;
(b) a targeting element facilitating cellular uptake and delivery of the therapeutic agent to a targeted adipocyte; and
(c) liposomal particles comprising sphingomyelin, DMPC, and cholesterol, wherein the liposomal particles enhance intra-cellular penetration of the therapeutic agent and protect the therapeutic agent from degradation.

2. The composition of claim 1, wherein sphingomyelin comprises 30-50% of the liposomal particles by weight, DMPC comprises 30-50% of the liposomal particles by weight, and cholesterol comprises 10-30% of the liposomal particles by weight.

3. The composition of claim 1, wherein sphingomyelin comprises 40% of the liposomal particles by weight, DMPC comprises 40% of the liposomal particles by weight, and cholesterol comprises 20% of the liposomal particles by weight.

4. The composition of claim 1, wherein the liposomes have a peak mean diameter between about 135 and 150 nm or a polydispersity index of less than about 0.035.

5. The composition of claim 1, wherein the therapeutic agent comprises an RNA oligonucleotide from 7 to 22 nucleotides in length.

6. The composition of claim 1, wherein the therapeutic agent comprises miR-22 antagomir, miR-515 agomir, dinitrophenol, niclosamide, (33 adrenergic receptor agonist, a thyromimetic agent, PPAR alpha agonist, PPAR gamma agonist, retinoic acid, hexarelin, thrombospondin-1 (TSP-1), prohibitin (PHB), a polyphenol, resveratrol, curcumin, a capsicinoid, an isoflavone, or a component of a gene editing system.

7. The composition of claim 1, wherein the targeting element is a lipid that is linked to the therapeutic agent.

8. The composition of claim 7, wherein the lipid comprises decanoic acid, dodecanoic acid, palmitic acid, stearic acid, oleic acid, oleoyl glycine, docosanoic acid, hexadecanoic acid, dotriacontahexaenoic acid, docosahexaenoic acid, or cholesterol.

9. The composition of claim 7, wherein the lipid is a fatty acid that is naturally transported by fatty acid translocase.

10. The composition of claim 5, wherein the therapeutic agent is encapsulated within the interior of the liposome.

11. The composition of claim 5, wherein the therapeutic agent is associated with the surface of the liposome.

12. The composition of claim 7, wherein the therapeutic agent is linked to the lipid by a linker selected from the group consisting of a covalent bond, a disulfide bond, a diester bond, a peptide bond, an ionic bond, or a biotin-streptavidin bond.

13. The composition of claim 1, wherein the targeting element specifically binds to Fatty Acid Translocase, Aquaporin 7, Perilipin 1, or Perilipin 2.

14. The composition of claim 13, wherein the targeting element comprises an antibody, antibody fragment, scFv, or single domain antibody.

15. The composition of claim 13, wherein the targeting element comprises hexarelin, or Thrombospondin-1, or a Thrombospondin-1 peptide having the amino acid sequence GVITRIR.

16. The composition of claim 13, wherein the therapeutic agent is linked to the targeting element by a linker selected from the group consisting of a covalent bond, a disulfide bond, a diester bond, a peptide bond, an ionic bond, or a biotin-streptavidin bond.

17. The composition of claim 1, wherein the therapeutic agent modulates lipid oxidation and/or respiratory chain uncoupling.

18. The composition of claim 17, wherein the therapeutic agent modulates activity of Uncoupling Protein 1, Uncoupling Protein 2, or Uncoupling Protein 3.

19. An adipocyte-targeting therapeutic agent comprising an oligonucleotide linked to Hexarelin via a disulfide bond.

20. The therapeutic agent of claim 19, wherein the oligonucleotide is between 7 and 22 nucleotides in length.

21. The therapeutic agent of claim 19, wherein the oligonucleotide is an antagomir of miR-22 or an agomir of miR-515.

22. A method of modulating thermogenic regulation in a subject comprising providing to the subject the composition of claim 1.

23. The method of claim 22, wherein providing the composition or therapeutic agent comprises administering the composition or therapeutic agent subcutaneously, transcutaneously or intravenously.

24. The method of claim 22, wherein the patient has obesity, type 2 diabetes mellitus, Non-Alcoholic Fatty Liver Disease, or Non-Alcoholic Steatohepatitis.

* * * * *